United States Patent
Sisken

(10) Patent No.: US 9,204,921 B2
(45) Date of Patent: Dec. 8, 2015

(54) RF ENERGY CONTROLLER AND METHOD FOR ELECTROSURGICAL MEDICAL DEVICES

(71) Applicant: Cook Medical Technologies LLC, Bloomington, IN (US)

(72) Inventor: Richard B. Sisken, Lafayette, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 149 days.

(21) Appl. No.: 13/713,648

(22) Filed: Dec. 13, 2012

(65) Prior Publication Data
US 2014/0171931 A1    Jun. 19, 2014

(51) Int. Cl.
*A61B 18/12* (2006.01)
*A61B 18/00* (2006.01)

(52) U.S. Cl.
CPC .......... *A61B 18/1206* (2013.01); *A61B 18/1233* (2013.01); *A61B 2018/00577* (2013.01); *A61B 2018/00642* (2013.01); *A61B 2018/00648* (2013.01); *A61B 2018/00678* (2013.01); *A61B 2018/00702* (2013.01); *A61B 2018/00708* (2013.01); *A61B 2018/00779* (2013.01); *A61B 2018/00827* (2013.01); *A61B 2018/00886* (2013.01); *A61B 2018/00892* (2013.01); *A61B 2018/00988* (2013.01)

(58) Field of Classification Search
None
See application file for complete search history.

(56) References Cited

U.S. PATENT DOCUMENTS

| | | |
|---|---|---|
| 4,231,372 A | 11/1980 | Newton |
| 4,301,801 A | 11/1981 | Schneiderman |
| 4,532,924 A | 8/1985 | Auth et al. |
| 4,651,280 A | 3/1987 | Chang et al. |
| 4,765,331 A | 8/1988 | Petruzzi et al. |
| 4,860,745 A | 8/1989 | Farin et al. |
| 4,898,169 A | 2/1990 | Norman et al. |
| 4,898,179 A | 2/1990 | Sirota |
| 4,959,710 A | 9/1990 | Uehara et al. |
| 5,162,725 A | 11/1992 | Hodson et al. |
| 5,244,462 A | 9/1993 | Delahuerga et al. |
| 5,350,376 A | 9/1994 | Brown |
| 5,383,874 A | 1/1995 | Jackson et al. |
| 5,400,267 A | 3/1995 | Denen et al. |

(Continued)

FOREIGN PATENT DOCUMENTS

| | | |
|---|---|---|
| EP | 1 366 724 A1 | 12/2003 |
| WO | WO 93/20770 A2 | 10/1993 |

(Continued)

OTHER PUBLICATIONS

International Search Report and Written Opinion for corresponding application No. PCT/US2013/074628 mailed May 15, 2014.

(Continued)

*Primary Examiner* — Kennedy Schaetzle
(74) *Attorney, Agent, or Firm* — Brinks Gilson & Lione

(57) ABSTRACT

A control unit controls delivery of RF energy generated by an RF generator to a medical device configured to perform a medical procedure. The control unit may be separate from the RF generator, and may have an input that may be attached to an output of the RF generator. The control unit includes switching circuitry that is closed while an amount of RF energy is transmitted through the control unit to the medical device. The switching circuitry opens when the amount of RF energy reaches a threshold level.

18 Claims, 11 Drawing Sheets

(56) References Cited

U.S. PATENT DOCUMENTS

| | | |
|---|---|---|
| 5,423,809 A | 6/1995 | Klicek |
| 5,425,375 A | 6/1995 | Chin et al. |
| 5,437,664 A | 8/1995 | Cohen et al. |
| 5,484,400 A | 1/1996 | Edwards et al. |
| 5,505,730 A | 4/1996 | Edwards |
| 5,520,684 A | 5/1996 | Imran |
| 5,558,619 A | 9/1996 | Kami et al. |
| 5,558,672 A | 9/1996 | Edwards et al. |
| 5,569,241 A | 10/1996 | Edwards |
| 5,575,788 A | 11/1996 | Baker et al. |
| 5,665,062 A | 9/1997 | Houser |
| 5,669,876 A | 9/1997 | Schechter et al. |
| 5,681,308 A | 10/1997 | Edwards et al. |
| 5,713,942 A | 2/1998 | Stern et al. |
| 5,735,847 A | 4/1998 | Gough et al. |
| 5,746,224 A | 5/1998 | Edwards |
| 5,769,846 A | 6/1998 | Edwards et al. |
| 5,800,429 A | 9/1998 | Edwards |
| 5,817,091 A | 10/1998 | Nardella et al. |
| 5,823,197 A | 10/1998 | Edwards |
| 5,827,273 A | 10/1998 | Edwards |
| 5,827,277 A | 10/1998 | Edwards |
| 5,843,020 A | 12/1998 | Tu et al. |
| 5,843,075 A | 12/1998 | Taylor |
| 5,843,077 A | 12/1998 | Edwards |
| 5,843,152 A | 12/1998 | Tu et al. |
| 5,846,236 A | 12/1998 | Lindenmeier et al. |
| 5,849,010 A | 12/1998 | Wurzer et al. |
| 5,868,737 A | 2/1999 | Taylor et al. |
| 5,871,481 A | 2/1999 | Kannenberg et al. |
| 5,876,369 A | 3/1999 | Houser |
| 5,897,553 A | 4/1999 | Mulier et al. |
| 5,899,917 A | 5/1999 | Edwards et al. |
| 5,902,328 A | 5/1999 | LaFontaine et al. |
| 5,913,856 A | 6/1999 | Chia et al. |
| 5,925,038 A | 7/1999 | Panescu et al. |
| 5,944,715 A | 8/1999 | Goble et al. |
| 5,948,009 A | 9/1999 | Tu |
| 5,954,649 A | 9/1999 | Chia et al. |
| 5,954,717 A | 9/1999 | Behl et al. |
| 5,957,920 A | 9/1999 | Baker |
| 5,957,922 A | 9/1999 | Imran |
| 5,964,727 A | 10/1999 | Edwards et al. |
| 5,964,755 A | 10/1999 | Edwards |
| 5,971,980 A | 10/1999 | Sherman |
| 5,980,517 A | 11/1999 | Gough |
| 5,991,355 A | 11/1999 | Dahlke |
| 6,002,968 A | 12/1999 | Edwards |
| 6,004,319 A | 12/1999 | Goble et al. |
| 6,006,755 A | 12/1999 | Edwards |
| 6,009,877 A | 1/2000 | Edwards |
| 6,013,074 A | 1/2000 | Taylor |
| 6,013,076 A | 1/2000 | Goble et al. |
| 6,015,406 A | 1/2000 | Goble et al. |
| 6,022,346 A | 2/2000 | Panescu et al. |
| 6,024,743 A | 2/2000 | Edwards |
| 6,027,501 A | 2/2000 | Goble et al. |
| 6,033,401 A | 3/2000 | Edwards et al. |
| 6,039,757 A | 3/2000 | Edwards et al. |
| 6,041,260 A | 3/2000 | Stern et al. |
| 6,044,846 A | 4/2000 | Edwards |
| 6,056,744 A | 5/2000 | Edwards |
| 6,056,745 A | 5/2000 | Panescu et al. |
| 6,056,746 A | 5/2000 | Goble et al. |
| 6,056,747 A | 5/2000 | Saadat et al. |
| 6,059,778 A | 5/2000 | Sherman |
| 6,063,081 A | 5/2000 | Mulier et al. |
| 6,066,139 A | 5/2000 | Ryan et al. |
| 6,068,653 A | 5/2000 | LaFontaine |
| 6,080,150 A | 6/2000 | Gough |
| 6,083,223 A | 7/2000 | Baker |
| 6,090,106 A | 7/2000 | Goble et al. |
| 6,092,528 A | 7/2000 | Edwards et al. |
| 6,093,186 A | 7/2000 | Goble |
| 6,113,592 A | 9/2000 | Taylor |
| 6,113,596 A | 9/2000 | Hooven et al. |
| 6,123,702 A | 9/2000 | Swanson et al. |
| 6,132,425 A | 10/2000 | Gough |
| 6,139,569 A | 10/2000 | Ingle et al. |
| 6,156,060 A | 12/2000 | Roy et al. |
| 6,165,206 A | 12/2000 | Tu |
| 6,168,594 B1 | 1/2001 | LaFontaine et al. |
| 6,174,308 B1 | 1/2001 | Goble et al. |
| 6,179,833 B1 | 1/2001 | Taylor |
| 6,183,468 B1 | 2/2001 | Swanson et al. |
| 6,190,382 B1 | 2/2001 | Ormsby et al. |
| 6,200,314 B1 | 3/2001 | Sherman |
| 6,217,576 B1 | 4/2001 | Tu et al. |
| 6,226,554 B1 | 5/2001 | Tu et al. |
| 6,233,477 B1 | 5/2001 | Chia et al. |
| 6,235,022 B1 | 5/2001 | Hallock et al. |
| 6,235,023 B1 | 5/2001 | Lee et al. |
| 6,236,891 B1 | 5/2001 | Ingle et al. |
| 6,237,604 B1 | 5/2001 | Burnside et al. |
| 6,245,065 B1 | 6/2001 | Panescu et al. |
| 6,245,067 B1 | 6/2001 | Tu et al. |
| 6,246,899 B1 | 6/2001 | Chia et al. |
| 6,254,598 B1 | 7/2001 | Edwards et al. |
| 6,258,087 B1 | 7/2001 | Edwards et al. |
| 6,259,941 B1 | 7/2001 | Chia et al. |
| 6,264,653 B1 | 7/2001 | Falwell |
| 6,266,551 B1 | 7/2001 | Osadchy et al. |
| 6,273,886 B1 | 8/2001 | Edwards et al. |
| 6,280,441 B1 | 8/2001 | Ryan |
| 6,287,303 B1 | 9/2001 | Geistert et al. |
| 6,293,942 B1 | 9/2001 | Goble et al. |
| 6,293,943 B1 | 9/2001 | Panescu et al. |
| 6,315,776 B1 | 11/2001 | Edwards |
| 6,322,558 B1 | 11/2001 | Taylor et al. |
| 6,322,584 B2 | 11/2001 | Ingle et al. |
| 6,325,798 B1 | 12/2001 | Edwards et al. |
| 6,346,104 B2 | 2/2002 | Daly et al. |
| 6,355,031 B1 | 3/2002 | Edwards et al. |
| 6,358,245 B1 | 3/2002 | Edwards et al. |
| 6,387,092 B1 | 5/2002 | Burnside et al. |
| 6,398,779 B1 | 6/2002 | Buysse et al. |
| 6,402,744 B2 | 6/2002 | Edwards et al. |
| 6,405,732 B1 | 6/2002 | Edwards et al. |
| 6,409,722 B1 | 6/2002 | Hoey et al. |
| 6,440,128 B1 | 8/2002 | Edwards et al. |
| 6,464,689 B1 | 10/2002 | Qin et al. |
| 6,464,697 B1 | 10/2002 | Edwards et al. |
| 6,468,204 B2 | 10/2002 | Sendai et al. |
| 6,475,216 B2 | 11/2002 | Mulier et al. |
| 6,488,678 B2 | 12/2002 | Sherman |
| 6,508,815 B1 | 1/2003 | Strul et al. |
| 6,517,535 B2 | 2/2003 | Edwards |
| 6,533,778 B2 | 3/2003 | Herzon |
| 6,535,768 B1 | 3/2003 | Baker et al. |
| 6,537,272 B2 | 3/2003 | Christopherson et al. |
| 6,551,310 B1 | 4/2003 | Ganz et al. |
| 6,562,034 B2 | 5/2003 | Edwards et al. |
| 6,587,750 B2 | 7/2003 | Gerbi et al. |
| 6,620,157 B1 | 9/2003 | Dabney et al. |
| 6,629,974 B2 | 10/2003 | Penny et al. |
| 6,641,580 B1 | 11/2003 | Edwards et al. |
| 6,645,201 B1 | 11/2003 | Utley et al. |
| 6,651,669 B1 | 11/2003 | Burnside |
| 6,652,514 B2 | 11/2003 | Ellman et al. |
| 6,660,002 B1 | 12/2003 | Edwards et al. |
| 6,663,625 B1 | 12/2003 | Ormsby et al. |
| 6,673,070 B2 | 1/2004 | Edwards et al. |
| 6,676,660 B2 | 1/2004 | Wampler et al. |
| 6,682,527 B2 | 1/2004 | Strul |
| 6,685,700 B2 | 2/2004 | Behl et al. |
| 6,689,127 B1 | 2/2004 | Gough et al. |
| 6,692,490 B1 | 2/2004 | Edwards |
| 6,712,074 B2 | 3/2004 | Edwards et al. |
| 6,712,814 B2 | 3/2004 | Edwards et al. |
| 6,723,091 B2 | 4/2004 | Goble et al. |
| 6,723,092 B2 | 4/2004 | Brown et al. |
| 6,730,077 B2 | 5/2004 | Carroll et al. |
| 6,730,079 B2 | 5/2004 | Lovewell |
| 6,733,495 B1 | 5/2004 | Bek et al. |

(56) References Cited

U.S. PATENT DOCUMENTS

| | | | |
|---|---|---|---|
| 6,736,810 | B2 | 5/2004 | Hoey et al. |
| 6,740,082 | B2 | 5/2004 | Shadduck |
| 6,783,523 | B2 | 8/2004 | Qin et al. |
| 6,790,206 | B2 | 9/2004 | Panescu |
| 6,790,207 | B2 | 9/2004 | Utley et al. |
| 6,796,981 | B2 | 9/2004 | Wham et al. |
| 6,802,841 | B2 | 10/2004 | Utley et al. |
| 6,805,128 | B1 | 10/2004 | Pless et al. |
| 6,808,525 | B2 | 10/2004 | Latterell et al. |
| 6,827,713 | B2 | 12/2004 | Bek et al. |
| 6,827,715 | B2 | 12/2004 | Francischelli et al. |
| 6,855,141 | B2 | 2/2005 | Lovewell |
| 6,872,206 | B2 | 3/2005 | Edwards et al. |
| 6,923,805 | B1 | 8/2005 | LaFontaine et al. |
| 6,929,641 | B2 | 8/2005 | Goble et al. |
| 6,936,024 | B1 | 8/2005 | Houser |
| 6,966,907 | B2 | 11/2005 | Goble et al. |
| 6,974,456 | B2 | 12/2005 | Edwards et al. |
| 6,984,231 | B2 | 1/2006 | Goble et al. |
| 6,994,704 | B2 | 2/2006 | Qin et al. |
| 7,004,938 | B2 | 2/2006 | Ormsby et al. |
| 7,008,421 | B2 | 3/2006 | Daniel et al. |
| 7,041,096 | B2 | 5/2006 | Malis et al. |
| 7,048,687 | B1 | 5/2006 | Reuss et al. |
| 7,056,320 | B2 | 6/2006 | Utley et al. |
| 7,070,595 | B2 | 7/2006 | Ormsby et al. |
| 7,122,031 | B2 | 10/2006 | Edwards et al. |
| 7,125,407 | B2 | 10/2006 | Edwards et al. |
| 7,137,980 | B2 | 11/2006 | Buysse et al. |
| 7,150,745 | B2 | 12/2006 | Stern et al. |
| 7,165,551 | B2 | 1/2007 | Edwards et al. |
| 7,195,627 | B2 | 3/2007 | Amoah et al. |
| 7,211,081 | B2 | 5/2007 | Goble |
| 7,214,224 | B2 | 5/2007 | Goble |
| 7,223,264 | B2 | 5/2007 | Daniel et al. |
| 7,250,050 | B2 | 7/2007 | Ryan |
| 7,258,688 | B1 | 8/2007 | Shah et al. |
| 7,278,991 | B2 | 10/2007 | Morris et al. |
| 7,282,048 | B2 | 10/2007 | Goble et al. |
| 7,282,049 | B2 | 10/2007 | Orszulak et al. |
| 7,293,563 | B2 | 11/2007 | Utley et al. |
| 7,300,436 | B2 | 11/2007 | Penny et al. |
| 7,300,437 | B2 | 11/2007 | Pozzato |
| 7,303,557 | B2 | 12/2007 | Wham et al. |
| 7,329,254 | B2 | 2/2008 | West et al. |
| 7,335,199 | B2 | 2/2008 | Goble et al. |
| 7,341,586 | B2 | 3/2008 | Daniel et al. |
| 7,344,532 | B2 | 3/2008 | Goble et al. |
| 7,344,535 | B2 | 3/2008 | Stern et al. |
| 7,353,068 | B2 | 4/2008 | Tanaka et al. |
| 7,364,577 | B2 | 4/2008 | Wham et al. |
| 7,367,974 | B2 | 5/2008 | Haemmerich et al. |
| 7,422,586 | B2 | 9/2008 | Morris et al. |
| 7,458,378 | B2 | 12/2008 | Utley et al. |
| 7,465,301 | B2 | 12/2008 | Bek et al. |
| 7,468,060 | B2 | 12/2008 | Utley et al. |
| 7,507,234 | B2 | 3/2009 | Utley et al. |
| 7,507,238 | B2 | 3/2009 | Edwards et al. |
| 7,520,877 | B2 | 4/2009 | Lee, Jr. et al. |
| 7,530,979 | B2 | 5/2009 | Ganz et al. |
| 7,553,309 | B2 | 6/2009 | Buysse et al. |
| 7,556,628 | B2 | 7/2009 | Utley et al. |
| 7,571,003 | B2 | 8/2009 | Pozzato |
| 7,585,296 | B2 | 9/2009 | Edwards et al. |
| 7,594,913 | B2 | 9/2009 | Ormsby et al. |
| 7,630,774 | B2 | 12/2009 | Karni et al. |
| 7,632,268 | B2 | 12/2009 | Edwards et al. |
| 7,648,500 | B2 | 1/2010 | Edwards et al. |
| 7,674,260 | B2 | 3/2010 | Sampson et al. |
| 7,689,292 | B2 | 3/2010 | Hadzic et al. |
| 7,699,842 | B2 | 4/2010 | Buysse et al. |
| 7,699,844 | B2 | 4/2010 | Utley et al. |
| 7,713,267 | B2 | 5/2010 | Pozzato |
| 7,780,662 | B2 | 8/2010 | Bahney |
| 7,785,322 | B2 | 8/2010 | Penny et al. |
| 7,803,156 | B2 | 9/2010 | Eder et al. |
| 7,862,564 | B2 | 1/2011 | Goble |
| 7,862,565 | B2 | 1/2011 | Eder et al. |
| 7,879,032 | B1 | 2/2011 | Garito et al. |
| 7,883,508 | B2 | 2/2011 | Thao et al. |
| 7,901,400 | B2 | 3/2011 | Wham et al. |
| 7,922,715 | B2 | 4/2011 | Qin et al. |
| 7,942,874 | B2 | 5/2011 | Eder et al. |
| 7,955,326 | B2 | 6/2011 | Paul et al. |
| 7,959,627 | B2 | 6/2011 | Utley et al. |
| 7,972,328 | B2 | 7/2011 | Wham et al. |
| 7,976,540 | B2 | 7/2011 | Daw et al. |
| 7,993,332 | B2 | 8/2011 | Goble et al. |
| 7,993,336 | B2 | 8/2011 | Jackson et al. |
| 7,993,338 | B2 | 8/2011 | Klimovitch et al. |
| 7,997,278 | B2 | 8/2011 | Utley et al. |
| 8,002,769 | B2 | 8/2011 | Goble et al. |
| 8,012,149 | B2 | 9/2011 | Jackson et al. |
| 8,062,290 | B2 | 11/2011 | Buysse et al. |
| 8,100,133 | B2 | 1/2012 | Mintz et al. |
| 8,104,956 | B2 | 1/2012 | Blaha |
| 8,133,222 | B2 | 3/2012 | Ormsby |
| 8,147,485 | B2 | 4/2012 | Wham et al. |
| 8,152,801 | B2 | 4/2012 | Goldberg et al. |
| 8,152,803 | B2 | 4/2012 | Edwards et al. |
| 8,192,426 | B2 | 6/2012 | Stern et al. |
| 8,197,476 | B2 | 6/2012 | Truckai |
| 8,197,477 | B2 | 6/2012 | Truckai |
| 8,206,381 | B2 | 6/2012 | Lischinsky et al. |
| 8,216,223 | B2 | 7/2012 | Wham et al. |
| 8,251,992 | B2 | 8/2012 | Utley et al. |
| 8,257,346 | B2 | 9/2012 | Qin et al. |
| 8,273,012 | B2 | 9/2012 | Wallace et al. |
| 8,277,495 | B2 | 10/2012 | Demetriou et al. |
| 8,298,226 | B2 | 10/2012 | Hosier |
| 8,303,583 | B2 | 11/2012 | Hosier et al. |
| 8,308,722 | B2 | 11/2012 | Ormsby et al. |
| 8,348,948 | B2 | 1/2013 | Bahney |
| 8,372,067 | B2 | 2/2013 | Woloszko et al. |
| 8,398,626 | B2 | 3/2013 | Buysse et al. |
| 8,398,627 | B2 | 3/2013 | Hosier |
| 8,409,174 | B2 | 4/2013 | Omori |
| 8,409,192 | B2 | 4/2013 | Asirvatham et al. |
| 8,439,908 | B2 | 5/2013 | Utley et al. |
| 8,452,383 | B2 | 5/2013 | Norris et al. |
| 8,486,065 | B2 | 7/2013 | Lee et al. |
| 8,568,405 | B2 | 10/2013 | Cox et al. |
| 8,574,229 | B2 | 11/2013 | Eder et al. |
| 8,597,287 | B2 | 12/2013 | Benamou et al. |
| 8,613,743 | B2 | 12/2013 | Selig |
| 8,636,736 | B2 | 1/2014 | Yates et al. |
| 8,641,704 | B2 | 2/2014 | Werneth et al. |
| 8,641,711 | B2 | 2/2014 | Kelly et al. |
| 8,646,460 | B2 | 2/2014 | Utley et al. |
| 8,657,817 | B2 | 2/2014 | Fischer et al. |
| 8,672,934 | B2 | 3/2014 | Benamou et al. |
| 8,685,016 | B2 | 4/2014 | Wham et al. |
| 8,685,018 | B2 | 4/2014 | Cox et al. |
| 8,696,662 | B2 | 4/2014 | Eder et al. |
| 8,702,690 | B2 | 4/2014 | Paul et al. |
| 8,702,694 | B2 | 4/2014 | Wallace et al. |
| 8,728,072 | B2 | 5/2014 | Eder et al. |
| 8,747,401 | B2 | 6/2014 | Gonzalez et al. |
| 8,771,269 | B2 | 7/2014 | Sherman et al. |
| 8,777,877 | B2 | 7/2014 | Stein et al. |
| 8,784,338 | B2 | 7/2014 | Wallace et al. |
| 8,821,486 | B2 | 9/2014 | Toth et al. |
| 8,822,875 | B2 | 9/2014 | Webster et al. |
| 8,838,206 | B2 | 9/2014 | Mohajer |
| 8,840,588 | B2 | 9/2014 | Clement et al. |
| 8,876,816 | B2 | 11/2014 | Hosier |
| 8,920,414 | B2 | 12/2014 | Stone et al. |
| 8,932,285 | B2 | 1/2015 | Morris et al. |
| 8,939,970 | B2 | 1/2015 | Stone et al. |
| 8,961,506 | B2 | 2/2015 | McCarthy et al. |
| 8,968,296 | B2 | 3/2015 | McPherson |
| 8,979,838 | B2 | 3/2015 | Woloszko et al. |
| 2003/0204185 | A1 | 10/2003 | Sherman et al. |
| 2004/0087936 | A1 | 5/2004 | Stern et al. |

(56) References Cited

U.S. PATENT DOCUMENTS

| | | |
|---|---|---|
| 2004/0215235 A1 | 10/2004 | Jackson et al. |
| 2004/0215296 A1 | 10/2004 | Ganz et al. |
| 2005/0096644 A1 | 5/2005 | Hall et al. |
| 2006/0079883 A1 | 4/2006 | Elmouelhi et al. |
| 2006/0224151 A1 | 10/2006 | Waaler |
| 2006/0235378 A1 | 10/2006 | Waaler |
| 2008/0015563 A1 | 1/2008 | Hoey et al. |
| 2008/0091195 A1 | 4/2008 | Sliwa et al. |
| 2008/0097422 A1 | 4/2008 | Edwards et al. |
| 2008/0103498 A1 | 5/2008 | West et al. |
| 2008/0172052 A1 | 7/2008 | Eder et al. |
| 2009/0012518 A1 | 1/2009 | Utley et al. |
| 2009/0036882 A1 | 2/2009 | Webster et al. |
| 2009/0048593 A1 | 2/2009 | Ganz et al. |
| 2009/0054889 A1 | 2/2009 | Newton et al. |
| 2009/0093805 A1 | 4/2009 | Bek et al. |
| 2009/0118699 A1 | 5/2009 | Utley et al. |
| 2009/0182321 A1 | 7/2009 | McGreevy et al. |
| 2009/0248019 A1 | 10/2009 | Falkenstein et al. |
| 2009/0254079 A1 | 10/2009 | Edwards et al. |
| 2009/0318914 A1 | 12/2009 | Utley et al. |
| 2010/0004648 A1 | 1/2010 | Edwards et al. |
| 2010/0042093 A9 | 2/2010 | Wham et al. |
| 2010/0057071 A1 | 3/2010 | Amoah et al. |
| 2010/0069942 A1 | 3/2010 | Shelton, IV |
| 2010/0087809 A1 | 4/2010 | Edwards et al. |
| 2010/0114087 A1 | 5/2010 | Edwards et al. |
| 2010/0121320 A1 | 5/2010 | Hosier et al. |
| 2010/0204694 A1 | 8/2010 | Mehta et al. |
| 2010/0274239 A1 | 10/2010 | Paul et al. |
| 2010/0331833 A1 | 12/2010 | Maschke et al. |
| 2011/0022041 A1 | 1/2011 | Ingle et al. |
| 2011/0071468 A1 | 3/2011 | Utley et al. |
| 2011/0087212 A1 | 4/2011 | Aldridge et al. |
| 2011/0098698 A1 | 4/2011 | Bek et al. |
| 2011/0112529 A1 | 5/2011 | Shikhman |
| 2011/0125146 A1 | 5/2011 | Greeley et al. |
| 2011/0172659 A1 | 7/2011 | Brannan |
| 2011/0178515 A1 | 7/2011 | Bloom et al. |
| 2011/0184404 A1 | 7/2011 | Walberg et al. |
| 2011/0190759 A1 | 8/2011 | Qin et al. |
| 2011/0202050 A1 | 8/2011 | Brewer et al. |
| 2011/0306960 A1 | 12/2011 | Eisele et al. |
| 2012/0004645 A1 | 1/2012 | Dastani |
| 2012/0004656 A1 | 1/2012 | Jackson et al. |
| 2012/0116156 A1 | 5/2012 | Lederman |
| 2012/0143177 A1 | 6/2012 | Avitall |
| 2012/0157838 A1 | 6/2012 | Adanny et al. |
| 2012/0157986 A1 | 6/2012 | Stone et al. |
| 2012/0158101 A1 | 6/2012 | Stone et al. |
| 2012/0165807 A1 | 6/2012 | Daw et al. |
| 2012/0203219 A1 | 8/2012 | Evans et al. |
| 2012/0209288 A1 | 8/2012 | Robinson |
| 2012/0239025 A1 | 9/2012 | Smith |
| 2012/0239028 A1 | 9/2012 | Wallace et al. |
| 2012/0283731 A1 | 11/2012 | Unger et al. |
| 2012/0283732 A1 | 11/2012 | Lam |
| 2012/0310311 A1 | 12/2012 | Elkah |
| 2013/0117669 A1 | 5/2013 | Shikhman et al. |
| 2013/0158634 A1 | 6/2013 | Ron Edoute et al. |
| 2013/0165916 A1 | 6/2013 | Mathur et al. |
| 2013/0165917 A1 | 6/2013 | Mathur et al. |
| 2013/0165918 A1* | 6/2013 | Riff .................. 606/35 |
| 2013/0165923 A1 | 6/2013 | Mathur et al. |
| 2013/0165924 A1 | 6/2013 | Mathur et al. |
| 2013/0165925 A1 | 6/2013 | Mathur et al. |
| 2013/0184701 A1* | 7/2013 | Dunning .................. 606/35 |
| 2013/0197503 A1 | 8/2013 | Orszulak |
| 2013/0197506 A1 | 8/2013 | Evans et al. |
| 2013/0197508 A1 | 8/2013 | Shikhman et al. |
| 2013/0211398 A1 | 8/2013 | Daw et al. |
| 2013/0226173 A1 | 8/2013 | Utley et al. |
| 2013/0231611 A1 | 9/2013 | Lischinsky et al. |
| 2013/0237979 A1 | 9/2013 | Shikhman et al. |
| 2013/0238062 A1 | 9/2013 | Ron Edoute et al. |
| 2013/0261613 A1 | 10/2013 | Norris et al. |
| 2013/0267943 A1 | 10/2013 | Hancock |
| 2013/0282085 A1 | 10/2013 | Lischinsky et al. |
| 2013/0304061 A1 | 11/2013 | Chang et al. |
| 2013/0317494 A1 | 11/2013 | Daw et al. |
| 2013/0345689 A1 | 12/2013 | Ruddenklau et al. |
| 2014/0018798 A1 | 1/2014 | Cox et al. |
| 2014/0025061 A1 | 1/2014 | Benamou |
| 2014/0058374 A1 | 2/2014 | Edmunds et al. |
| 2014/0058382 A1 | 2/2014 | Yang |
| 2014/0073858 A1 | 3/2014 | Sherwinter |
| 2014/0074090 A1 | 3/2014 | Lam et al. |
| 2014/0148802 A1 | 5/2014 | LeMay |
| 2014/0155882 A1 | 6/2014 | Cox et al. |
| 2014/0163359 A1 | 6/2014 | Sholev et al. |
| 2014/0163549 A1 | 6/2014 | Yates et al. |
| 2014/0207217 A1 | 7/2014 | Lischinsky et al. |
| 2014/0236139 A1 | 8/2014 | Payman |
| 2014/0238175 A1 | 8/2014 | Huszar et al. |
| 2014/0238176 A1 | 8/2014 | Huszar et al. |
| 2014/0276749 A1 | 9/2014 | Johnson |
| 2014/0276753 A1 | 9/2014 | Wham et al. |
| 2014/0276754 A1 | 9/2014 | Gilbert et al. |
| 2014/0288546 A1 | 9/2014 | Sherman et al. |
| 2014/0296629 A1 | 10/2014 | Chang et al. |
| 2014/0296846 A1 | 10/2014 | Huszar et al. |
| 2014/0296848 A1 | 10/2014 | Chang et al. |
| 2014/0296902 A1 | 10/2014 | Huszar et al. |
| 2014/0330353 A1 | 11/2014 | Knight |
| 2014/0336632 A1 | 11/2014 | Toth et al. |
| 2014/0336636 A1 | 11/2014 | Huszar et al. |
| 2014/0350564 A1 | 11/2014 | Huszar et al. |
| 2015/0032094 A1 | 1/2015 | Kane et al. |
| 2015/0032100 A1 | 1/2015 | Coulson et al. |

FOREIGN PATENT DOCUMENTS

| | | |
|---|---|---|
| WO | WO 95/09577 A1 | 4/1995 |
| WO | WO 2006/017666 A2 | 2/2006 |

OTHER PUBLICATIONS

B.J. Dunkin et al., "Thin-layer ablation of human esophageal epithelium using a bipolar radiofrequency balloon device", Surgical Endoscopy (2006) 20; 125-130.

R.M. Bremner et al, "Ultrasonic epithelial ablation of the lower esophagus without stricture formation", Surgical Endoscopy (1998) 12; 342-347.

C.P. Barham et al., "Photothermal laser ablation of Barrett's oesophagus: endoscopic and histological evidence of squamous re-epithelialisation", Gut (1997); 41: 281-284.

\* cited by examiner

RF ENERGY CONTROLLER AND METHOD FOR ELECTROSURGICAL MEDICAL DEVICES

TECHNICAL FIELD

The present invention relates generally to medical devices, and more particularly to control units that control the delivery of radio frequency (RF) energy to medical devices.

BACKGROUND

Barrett's esophagus is an abnormal change in the cells in a lower or bottom portion of the esophagus, which may be due to the esophagus receiving too much acid from the stomach. In some cases, the abnormal change may lead to cancer. To treat Barrett's esophagus, radio frequency (RF) energy, such as RF pulses, may be applied to skin cells or tissue at the surface of the esophagus. The application of the RF energy may ablate the tissue.

To ablate only the targeted tissue (i.e., the tissue at the surface), the RF pulses may be intense and short in duration. RF energy is typically not applied for longer than one second, and in many cases about one-half second or less. The duration that the RF energy is applied to the treatment site may be critical. Too much RF energy may cause harm to the patient, such as excessive burning of the tissue. Conversely, too little RF energy may fail to treat all of the abnormal skin cells. However, the duration of application of the RF energy may be difficult to control, particularly where the application is controlled through activation of a foot pedal.

Some RF generators may include and/or be housed with monitoring devices that monitor characteristics of the RF energy being output by the RF generator to prevent too much power from being output. Such monitoring devices may include digital processors and controls that are within the RF generators. However, many hospitals or other facilities have conventional RF generators that are not equipped with the monitoring devices. As such, a controller or control unit that is attachable to an RF generator and that controls delivery of RF energy from the generator to the medical device may be desirable.

BRIEF SUMMARY

The present disclosure describes a control unit that is configured to control delivery of radio frequency (RF) energy to a medical device. The control unit may include switching circuitry configured to switch between a closed state and an open state. In the closed state, the switching circuitry may be configured to permit RF energy received from an RF generator to be output by the control unit to the medical device. In the open state, the switching circuitry may be configured to prevent RF energy from being output by the control unit to the medical device. The control unit may also include energy measurement circuitry configured to measure an amount of RF energy delivered to the medical device; and switch the switching circuitry from the closed state to the open state when the amount of RF energy delivered to the medical device reaches a predetermined RF energy level.

The present disclosure also describes a method to control transmission of radio frequency (RF) energy from a RF generator to a medical device with a control unit coupled to the RF generator and the medical device. The method includes configuring switching circuitry of the control unit in a closed state. The method further includes receiving, with the switching circuitry in the closed state, RF energy from the RF generator; and transmitting, with the switching circuitry in the closed state, the RF energy to an output of the control unit. The method also includes determining, with energy measurement circuitry, the RF energy in the RF energy delivered to the medical device; and switching the switching circuitry, from the closed state to an open state upon the determined RF energy reaching a predetermined threshold energy level.

The present disclosure further describes a control unit configured to control delivery of radio frequency (RF) energy. The control unit includes an output coupled to a medical device configured to perform an ablation procedure; and an input coupled to an output of a RF generator configured to supply RF energy to the medical device for the ablation procedure. The control unit further includes switching circuitry coupled to the input and the output. The switching circuitry may be configured to permit the control unit to output RF energy received from the RF generator in a closed state, and to prevent the control unit from outputting the RF energy received from the RF generator in an open state. The switching circuitry may also include energy measurement circuitry coupled to the output. The energy measurement circuitry may be configured to determine an amount of RF energy being delivered to the medical device. The energy measurement circuitry may also be configured to switch the switching circuitry from the closed state to the open state when the amount of RF energy reaches a threshold level.

DETAILED DESCRIPTION

The present description describes a control unit that controls delivery of radio frequency (RF) energy to a medical device. The control unit may have an input or an input connector that is coupled to an output or an output connector of an RF generator that supplies RF energy for a medical procedure, such as tissue ablation. The control unit may receive RF energy and send the RF energy to a medical device that delivers the RF energy to a treatment site within a patient to perform the medical procedure. The control unit may measure the RF energy being delivered to the treatment site and determine when the RF energy reaches a predetermined level. When the RF energy reaches the predetermined RF energy level, the control unit may prevent further RF energy from being delivered to the medical device.

The predetermined RF energy level may be a selected amount of energy to be delivered to the treatment site for performing the medical procedure. When more than the predetermined RF energy level is delivered, harm or injury may be caused to the patient, such as burning of tissue at the treatment site. Alternatively, when less that the predetermined RF energy level is delivered, the medical procedure may be unsatisfactorily performed, such as by ablating an insufficient amount of tissue. As such, the control unit may be and/or provide a control and safety mechanism for the RF generator.

The control unit may be used with a conventional RF generator, such as a conventional electrosurgical unit (ESU), that does not include and/or have "built-in" similar control and safety mechanisms. The control unit may be a component separate to the RF generator. For example, the control unit may include a structure or "box" that is not housed within a housing the RF generator. Instead, the control unit may be housed outside of the RF generator. The control unit may have an input that may be connected or coupled to an output of the RF generator. Before performing the medical procedure, the control unit may be attached to the output of the RF generator. After the medical procedure is performed, the control unit may be detached from the output of the RF generator.

The housing of the control unit may be an enclosed structure that is configured to house circuitry and/or various circuit elements that measure the RF energy and determine when the RF energy reaches the predetermined level. The circuits may be hardware and/or analog circuits comprised of analog components that perform analog operations. The circuitry of the control unit may not include digital circuitry such as microprocessors, integrated circuits or other circuits that perform digital operations and/or execute software to perform energy measurement and timing operations.

Figure 1:
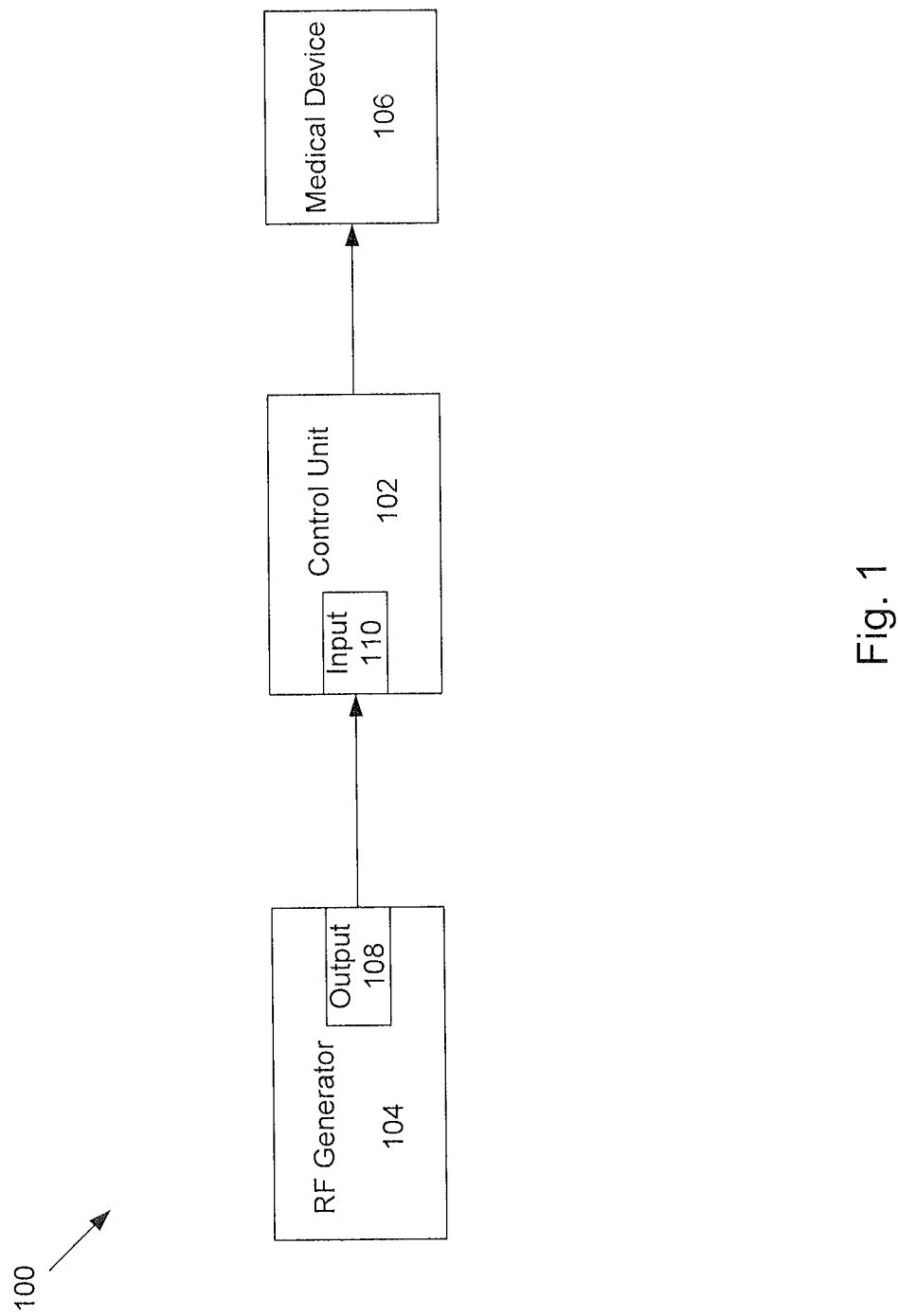
FIG. 1 shows a block diagram of a control unit coupled to a radio frequency (RF) generator and a medical device.

FIG. 1 shows a schematic diagram of an example medical system 100 that includes a control unit 102 that is configured to control delivery of RF energy from a RF generator 104 to a medical device 106. The RF generator 104, such as an electrosurgical unit (ESU), may be configured to supply the RF energy The RF energy may have characteristics, such as waveform, frequency, waveform, power, and/or amplitude characteristics, to perform an electrosurgical medical procedure, such as ablation or coagulation. To perform tissue ablation, for example, the RF energy may be a sine wave (such as a pulsed sine wave) having a frequency in a range of about 400 to 480 kilohertz (kHz), and a power of about 12 to 15 Watts. Other waveform, frequency, power, and/or amplitude characteristics may be used, which may depend on the medical procedure being performed.

The RF generator 104 may include an output 108 that may be configured to supply the RF energy to the connected system 100. In some example configurations, the output 108 may be a bipolar output connector. The type of connector may depend on the medical procedure being performed and/or the medical device 106 being used to perform the medical procedure. In addition or alternatively, the RF generator 104 may include and/or be adapted to connect to an input device (not shown), such as a foot pedal, that is used to generate the RF signals. The input device may be operated by the physician performing the medical procedure. For example, to generate the RF signals, the physician may activate and/or engage the input device. To cease generation of the RF signals, the physician may deactivate or disengage from the input device.

The control unit 102 may include an input 110 that is configured to connect to, attach to, and/or engage with the output 108 of the RF generator 104. When connected, attached, and/or engaged to the output 108, the control unit 102 may receive the RF energy from the RF generator 104. In some configurations, the input 110 may be removably attachable and/or connected to the output 108. For example, the input connector 110 may be attached or connected to the output connector 108, then detached or disconnected from the output connector 108, then reattached or reconnected to the output connector 108, and so on. The input connector 110 may be of any type or of any configuration that can connect and/or engage with the output connector 108 of the RF generator. In some configurations, the input connector 110 may be a banana connector or plug, although other types may be used and may depend on the configuration of the output connector 108 to which the input connector 110 is configured to connect.

The control unit 102 may be configured to switch between a closed state and an open state. When the control unit 102 is in the closed state, the control unit 102 may be configured to send the RF energy that the control unit 102 receives from the RF generator 104 to the medical device 106. In the open state, the control unit 102 may be configured to prevent the RF energy that the control unit 102 receives from the RF generator 104 from being sent to the medical device 106.

The control unit 102 may be configured to switch between the closed state and the open state by measuring an amount of energy being supplied to the medical device 106 from the RF generator 104. As the control unit 102 passes the RF energy that it receives from the RF generator 104 to the medical device 106, the amount of RF energy being supplied to the medical device 106 may increase to a threshold level. When the amount of RF energy is below the threshold level, the control unit 102 may be configured in the closed state, allowing the RF energy to be passed to the medical device 106. When the amount of RF energy reaches the threshold level, the control unit 102 may be configured to switch from the closed state to the open state, preventing the RF energy to be passed to the medical device 106.

The medical device 106 may include one or more components used to perform an electrosurgical medical procedure. For example, the medical device 106 may include one or more electrodes and/or one or more patches of electrode elements that are configured to receive the RF energy and provide the RF energy to a treatment site, such as tissue within a patient. The medical device 106 may further include a catheter or other elongate tubular body that may deliver the electrodes to the treatment site. In one example, the medical device 106 may be configured to treat Barrett's Esophagus and/or deliver RF energy in order to ablate tissue in the patient's esophagus.

Figure 2:
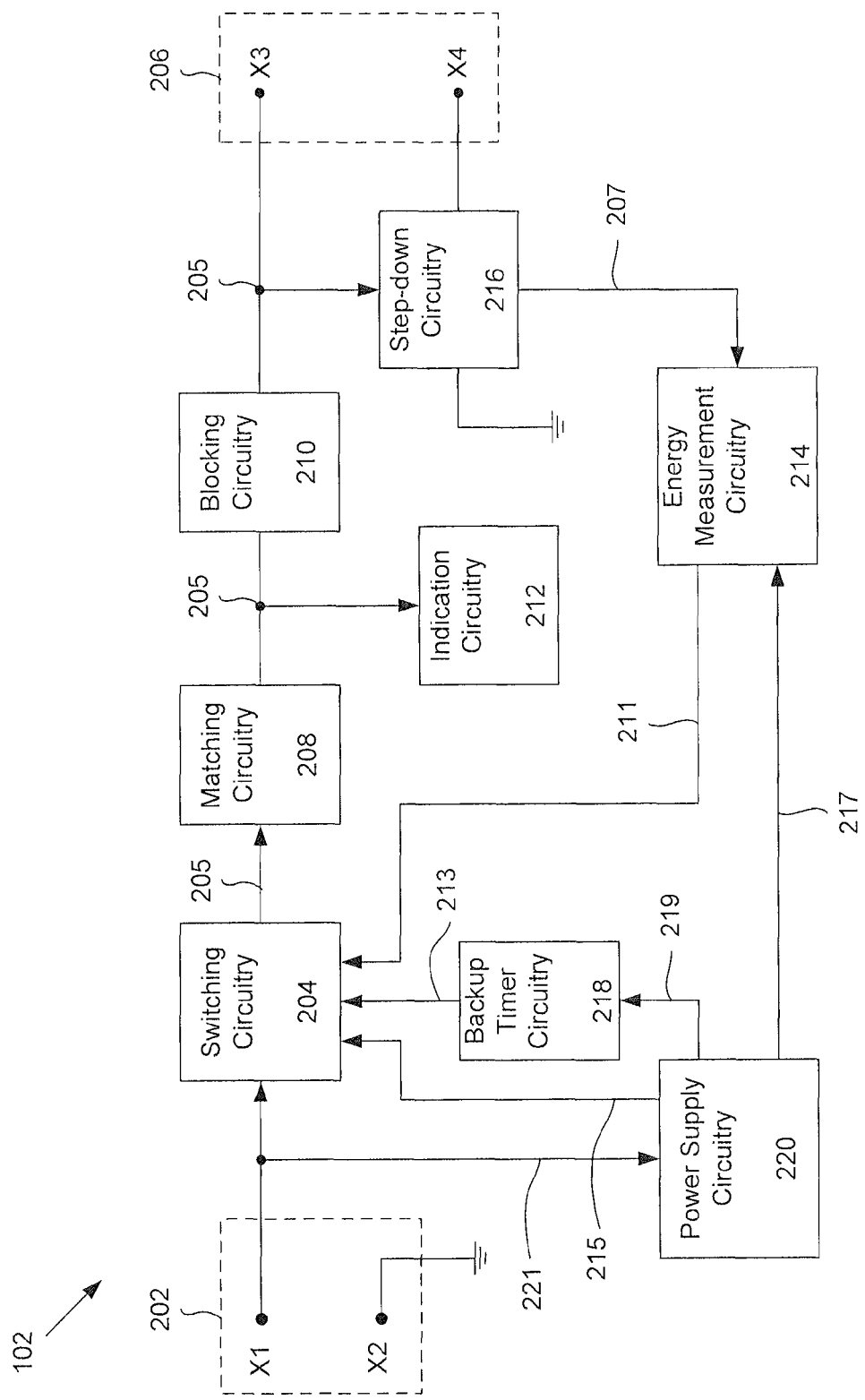
FIG. 2 shows a block diagram of the control unit.

FIG. 2 shows a block diagram of the control unit 102 in more detail. The control unit 102 may include an input 202 that is configured to receive RF energy from the RF generator 104. The input 202 may include a pair of terminals X1, X2, which may be configured or adapted to be connected to an output of the RF generator 104. For example, the terminals X1, X2 may be configured to be connected to a bipolar output of the RF generator 104. As shown in FIG. 2, one of the terminals X2 may be connected to a circuit ground. The other terminal X1 may be coupled to switching circuitry 204 and power supply circuitry 206.

The switching circuitry 204 may be configured to switch between a closed state and an open state, which in turn, may switch the control unit 102 between the closed state and the open state. When the switching circuitry 204 is in the closed state, the switching circuitry 204 may transmit the RF energy received from the input 202 along an output path 205 to an output 206 of the control unit 102. As shown in FIG. 2, the RF energy may pass through matching circuitry 208 and blocking circuitry 210 along the output path 205 before being provided to the output 206. Additionally, a small portion of the RF energy may be provided to indication circuitry 212 and energy measurement circuitry 214 via step-down circuitry 216 before being sent to the output 206. Alternatively, when the switching circuitry 204 is in the open state, the switching circuitry 201 may block or prevent transmission of the RF energy to the output 206 of the control unit 102.

As shown in FIG. 2, the output 206 may include a pair of terminals X3, X4 that are configured to be connected to the medical device 106 and provide RF energy to the medical device 106.

The matching circuitry 208, which may or may not be included or needed as a component of the control unit 102, may be used or configured to match the impedance of the load on the output 206 with the output impedance of the RF generator 104. In some example configurations, the matching circuitry 208 may include a matching transformer having a primary and secondary turns ratio to achieve the desired impedance matching.

In some situations, the impedance of the load at the output 206, which may be the impedance of the patient's tissue, may be about 25 ohms, and the load at the input, which may be the impedance of the output load of the RF generator 104, may be about 125 ohms, requiring an impedance change of a factor of about five. In these situations, the matching transformer may have 8 primary turns and 6 secondary turns, or if configured as an autotransformer, 14 primary turns and 6 secondary turns, which yields a turns ratio of about 2.3, or an impedance change of slightly over 5 (i.e., the turns ratio squared).

The blocking circuitry 210, which may or may not be included or needed as a component of the control unit 102, may be used or configured to block or prevent direct current (DC) and/or low-frequency components of the RF energy from being communicated to the output 206. The blocking circuitry 210 may be included because these RF signal components may cause harm to the patient during treatment. For example, low frequency components may shock the heart, which is located near the esophagus. The blocking circuitry 210 may include a capacitors coupled in series with the matching circuitry 208, and terminal X3 of the output 206, although other or additional circuitry may be used to block DC and/or low frequency components of the RF energy. To meet international standards, the blocking capacitor C2 may be less than 50 nF.

The indication circuitry 212, which may or may not be included as a component of the control unit 102, may be configured to output an indication that RF energy is being supplied to the medical device 106. In one example embodiment, the indication circuitry 212 includes a light emitting diode (LED) that outputs a light signal or is "on" when the RF signals are being sent to the output 206 and does not output a light signal or is "off" when RF energy is not being supplied to the output 206. In alternative example embodiments, the indication circuitry 212 may include circuitry in addition to or other than an LED, such as a speaker or a display device that outputs an audio and/or a visual signal to indicate whether RF energy is being supplied to the medical device 106. The indication circuitry 212 may be useful to and/or used by an operator of the RF generator 104, which may identify when to cease application of the RF energy (e.g., by removing bias on a foot pedal or other RF actuator) by observing the indication, such as when the LED turns from "on" to "off." The indication circuitry 214 may be coupled in shunt to the output path 205, and as shown in FIG. 2, may be coupled in shunt in between the matching circuitry 208 and the blocking circuitry 210. By being coupled in shunt, a small portion of the RF energy in the RF signals being supplied to the output 206 may be diverted to the indication circuitry 212, which the indication circuitry 212 may use to output the indication.

As shown in FIG. 2, the step-down circuitry 216 may be coupled in shunt to the output path 205 between the blocking circuitry 210 and the output 206. The step-down circuitry 216 may include a resistive network comprising one or more resistors. Based on the portion of the RF energy that the step-down circuitry 216 receives, the step-down circuitry 216 may be configured to provide one or more signals indicative of and/or proportional to the amount of RF energy being supplied to the output 206 and medical device 106. The step-down circuitry 216 may be configured to send the signals indicative of the supplied RF energy via connection 207 to the energy measurement circuitry 214. The connection 207 may include a plurality of connections configured to send a plurality of signals to the energy measurement circuitry 214. The plurality of signals may include signals indicative of, representative of, and/or proportional to the voltage and current being supplied to the medical device 106, which may then be used to generate signals indicative of the supplied RF energy. The step-down circuitry 216 may be coupled to both of the output terminals X3, X4 to generate the signals.

The energy measurement circuitry 214 may be configured to measure an amount of energy, such as an amount of total energy that is being supplied to the medical device 106 via the output 206. The energy measurement circuitry 214 may further be configured to determine when the amount of RF energy reaches a threshold level. The threshold level may be a predetermined level and/or may indicate an energy level that, when met, may be a sufficient portion of a medical treatment. The energy measurement circuitry 214 may be coupled to the switching circuitry 204 via connection 211 such that when the amount of energy reaches the threshold level, the energy measurement circuitry 214 may cause the switching circuitry 204 to switch from the closed state to the open state, which may prevent RF energy received from the RF generator 104 from being sent to the medical device 106.

The control unit 102 may further include backup timer circuitry 218. The backup timer circuitry 218 may be configured to switch the switching circuitry 204 from the closed state to the open state when a period of time elapses. For example, the backup timer circuitry 218 may be coupled to the switching circuitry 204 via a connection 213, such that when the period of time elapses, the backup timer circuitry 218 may cause the switching circuitry 204 to switch from the closed state to the open state, preventing RF energy received from the RF generator 104 from being sent to the medical device 106.

In some configurations, the period of time may be a predetermined period of time that is greater than an expected and/or an anticipated period of time for the RF energy being supplied to the medical device 104 to reach the threshold level. In this sense, the backup timer circuitry 218 may function as a safety feature of the control unit 102. In particular, the backup timer circuitry 218 may ensure that RF energy may not be supplied to the treatment site for an extended period of time such that harm may be caused to the patient, particularly if the switching circuitry 204 does not switch from the closed state to the open state when the supplied RF energy reaches the threshold level. If the switching circuitry 204 does not switch when the RF energy reaches the threshold level—such as due to a malfunction or failure by the energy measurement circuitry 214 and/or by the switching circuitry 204—then the backup timer circuitry 218 may serve as backup or secondary control circuitry that turns the switching circuitry 204 to the open state. When the backup timer circuitry 218 switches the switching circuitry 204 to the open state, the backup timer circuitry 218 may prevent the RF energy from being supplied to the treatment site for too long of a period of time. In one example, the predetermined period of time may be about one second, which may be greater than an expected and/or anticipated period of time of about 0.5 seconds for the supplied RF energy to reach the threshold level.

The control unit 102 may further include power supply circuitry 220. As shown in FIG. 2, the power supply circuitry 220 may be coupled to the input terminal X1 via a connection 221. A portion of the RF energy received from the RF generator 104 by the input 202 may be sent to the power supply circuitry 220, and a remaining portion may be sent to the switching circuitry 204. The portion of the RF energy sent to the power supply circuitry 220 may be used by the power supply circuitry 220 to power active elements of the circuitry components of the control unit 102. In this way, the control unit 102 may be a self-powering device or apparatus in that the control unit 102 does not receive power from a separate power supply. Instead, the control unit 102 may power itself by generating its own power, using the RF energy that the control unit 102 receives from the RF generator 104.

Figure 3:
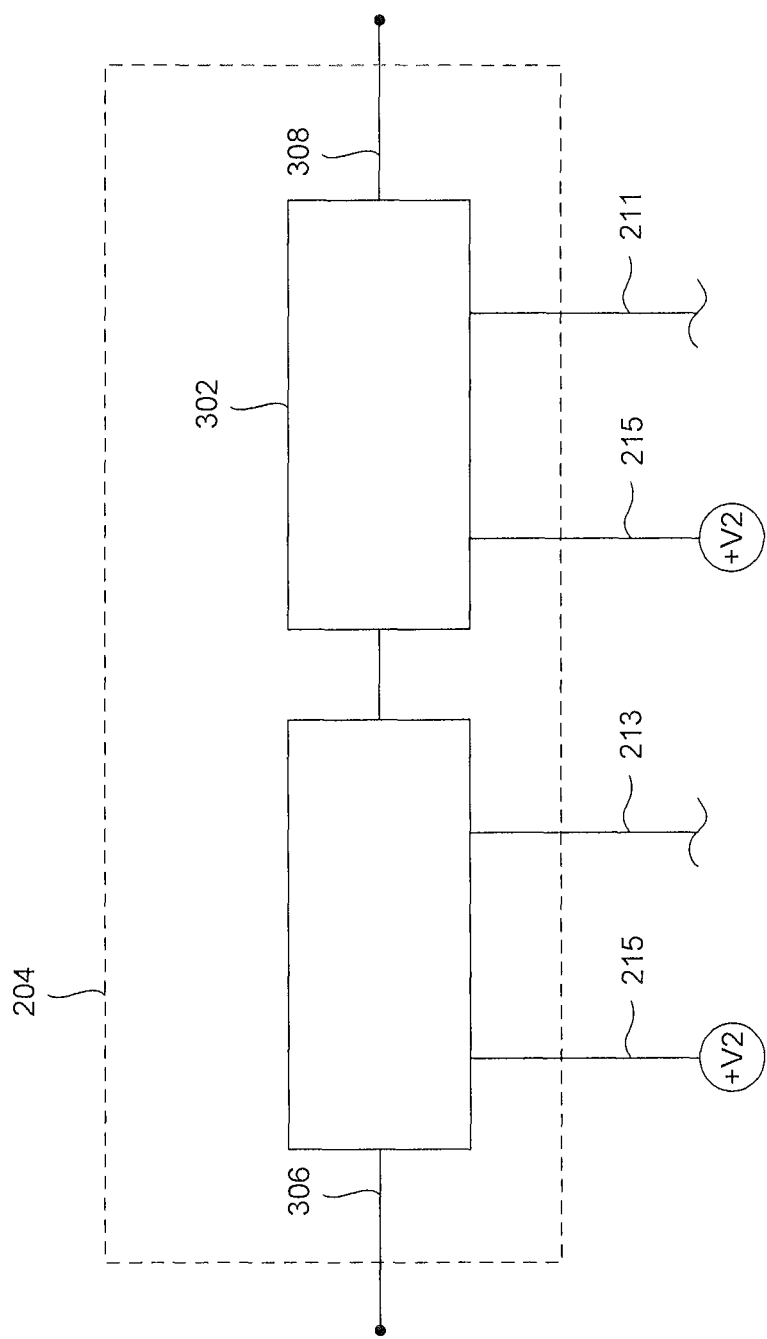
FIG. 3 shows a circuit diagram of example switching circuitry in the control unit.

FIG. 3 shows a circuit diagram of an example circuit configuration of the switching circuitry 204. The switching circuitry 204 may include a first switch 302 connected in series with a second switch 304. The switches 302 may switch the switching circuitry 204 between the closed state and the open state when the energy measurement circuitry 214 detects that the RF energy being supplied to the medical device 106 has reached the threshold level. The other switch 304 may switch the switching circuitry 204 between the closed state and the open state when the period of time determined by the backup timer circuitry 218 elapses. For example, the first switch 302 may be coupled to the energy measurement circuitry 214 via connection 211 such that when the amount of energy supplied to the medical device 106 reaches the threshold level, the energy measurement circuitry 214 may cause the first switch 302 to switch from a closed state to an open state, which in turn may configure the switching circuitry 204 in the open state and prevent RF energy from being supplied to the medical device 106. The second switch 304 may be coupled to the backup timer circuitry 218 via connection 213 such that when a period of time determined by the backup timer circuitry 218 elapses, the backup timer circuitry 218 may cause the second switch 304 to switch from a closed state to an open state, which in turn may configure the switching circuitry 204 in the open state and prevent RF energy from being output from the control unit 102. By being connected in series, only one, or alternatively both, of the switches 302, 304 may be in the open state to configure the switching circuitry 204 in the open state and prevent RF energy from being supplied to the medical device 106.

The switching circuitry 204 may further include an input 306 coupled to the input 202 of the control unit 102 and the second switch 304, and an output 308 coupled to the output path 205 and the first switch 302. When both the first switch 302 and the second switch 304 are in the closed state, the RF signals received from the input 202 of the control unit 102 may be communicated from the input 306, through the second switch 304 and the first switch 302, to the output 308.

In some example embodiments, the first switch 302 and/or the second switch 304 may be relays. In a preferred embodiment, the relays 302 and 304 may be double pole double throw relays, although in alternative embodiments, one or both of the relays 302, 304 may be a different type, such as single pole single throw, single pole double throw, or double pole single throw, as examples.

The first relay 302 may be coupled to the energy measurement circuitry 214 via the connection 211. The energy measurement circuitry 214 may be configured to activate the first relay 302 when the energy measurement circuitry 214 detects that the RF energy being supplied to the medical device 106 has reached the threshold level, which may switch the first relay from the closed state to the open state. The first relay 302 may also receive a positive power supply signal +V2 to activate the first relay 302. The second relay 304 may be coupled to the backup timer circuitry 218 via the connection 213. In some configurations, when the period of time elapses, the backup timer circuitry 218 may activate the second relay 304, which may switch the second relay 304 from the closed state to the open state. In alternative configurations, the second relay 304 may be in the closed state when activated by the backup timer circuitry 218. In these alternative configurations, the backup timer circuitry 218 may activate the second relay 304 to maintain the second relay 304 in the closed state until the time period elapses, at which point the backup timer circuitry 218 may deactivate the second relay 304 to switch the second relay 304 to the open state. The first relay 302 may also receive the positive power supply signal +V2 to activate the first relay 302.

The switching circuitry 204 is not limited to using double pole double throw relays, and alternative embodiments may include other types of relays that switch from being closed to being open when activated may be used. However, the use of relays having two poles may provide extra safety compared to single pole relays in that when the electromagnetic device is activated, if one pole opens but the other pole malfunctions and remains closed, the relay is still switched to the open state. In other words, both poles must malfunction for the switch to stay closed. In other alternative embodiments, the switching circuitry 202 may include switches or switching devices other than relays, such transistors or other semiconductor and/or solid state devices.

Figure 4:
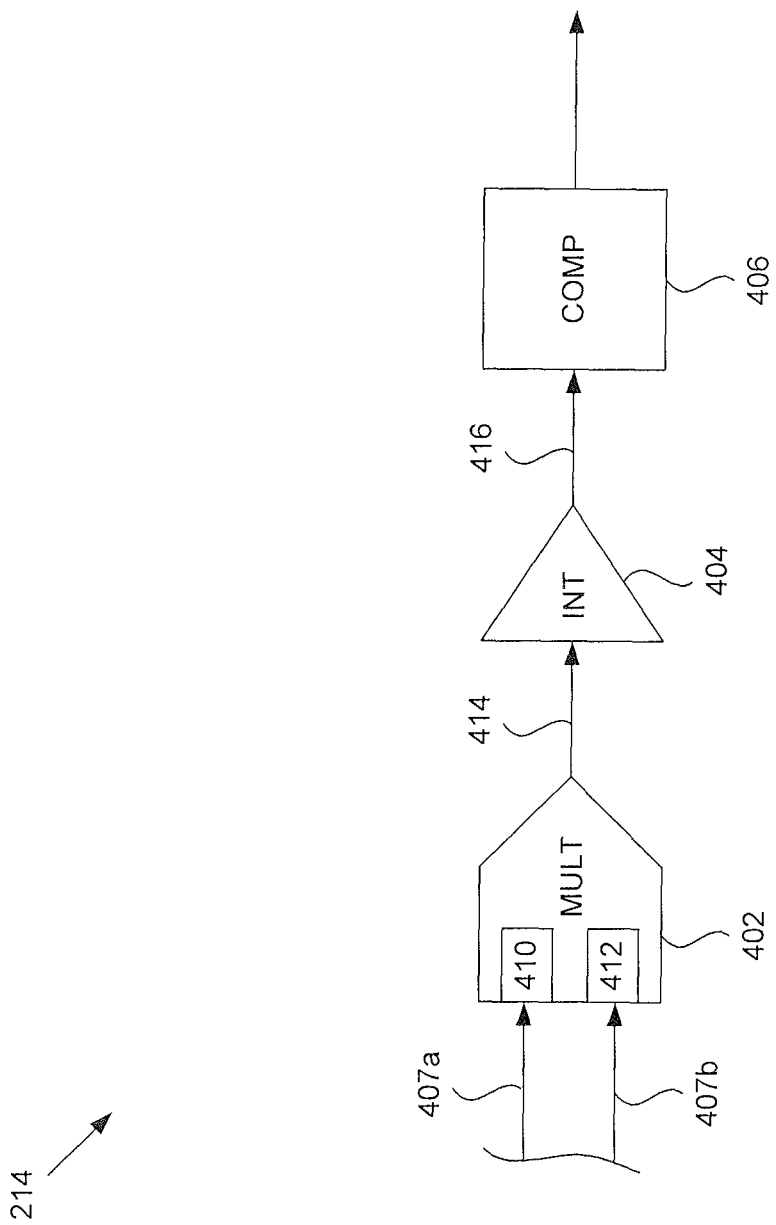
FIG. 4 shows a block diagram of example energy measurement circuitry in the control unit.

FIG. 4 shows a block diagram of the energy measurement circuitry 214 of the control unit 102 in more detail. The energy measurement circuitry 214 may be configured to determine an amount of RF energy, such as an amount of total RF energy, that is supplied to the medical device 106. The energy measurement circuitry 214 may also determine whether the amount of RF energy has reached a threshold level, and in response to the determination, may generate and/or output a signal that switches the switching circuitry 204 from the closed state to the open state. To perform these actions or functions, the energy measurement circuitry 214 may include three main circuit elements—multiplier circuitry 402, integrator circuitry 404, and comparator circuitry 406.

The multiplier circuitry 402 may include inputs 410, 412, which may be coupled to the output path 205 via the step down-circuitry 216 and the connection 207. As previously described, the connection 207 may include multiple connections configured to supply a plurality of signals to the energy measurement circuitry 214 that are indicative of, representative of, and/or proportional to the voltage and current being supplied to the medical device 106. As shown in FIG. 4, the connection 207 may include a first connection 407a and a second connection 407b. In one example configuration, signals proportional to the voltage being output from the control unit 102 and/or supplied to the medical device 106—hereinafter referred to as voltage signals—may be sent to the first input 410 via the first connection 407a. Signals proportional to the current being output from the control unit 102 and/or supplied to the medical device 106—hereinafter referred to as current signals—may be sent to the second input 412 via the second connection 407b. The multiplier circuitry 402 may be configured to multiply the voltage signals with the current signals. Based the multiplication of the voltage signals and the current signals, the multiplier circuitry 402 may be configured to generate a signal indicative of instantaneous power being supplied to the medical device 106.

The multiplier circuitry 402 may be configured to output the signal indicative of the instantaneous power to the integrator circuitry 404 via a connection 414. The integrator circuitry 404 may be configured to receive the signal output from the multiplier circuitry 402 or receive signals based on the signals output from the multiplier circuitry 402, such as signals that are scaled down from the signals output from the multiplier circuitry 402. Upon receipt, the integrator circuitry 404 may be configured to generate and output signals indicative of the average power or total energy being supplied to the medical device 106.

The comparator circuitry 406 may be configured to receive the signals output from the integrator circuitry 404 or receive signals based on the signals from the integrator 404, such as signals that are scaled down from the signals output from the integrator circuitry 404. Upon receipt, the comparator circuitry 406 may be configured to compare the received signals with a reference value, such as a predetermined reference value, proportional to a threshold energy level, the threshold energy level being a RF energy level that corresponds to a portion of the treatment. By comparing the received signals with the reference value, the comparator circuitry 406 may be configured to determine whether the RF energy being supplied to the medical device 106 is below or has reached the threshold energy level.

Based on the comparison of the signals received from the integrator circuitry 406 and the reference value, the comparator circuitry 406 may output a signal that switches the switching circuitry 204, including the first switch 302, between the closed and open states. For example, when the comparator circuitry 406 determines that the received signal is less than or does not exceed the reference value, the comparator circuitry 406 may be configured to not output a signal, or alternatively may be configured to output a signal at a level that configures the first switch 302 in the closed state. In particular, the comparator circuitry 406 may not output a signal, or alternatively may output a signal at a level that does not induce current through the electromagnetic device 310 (FIG. 3), which positions the first switch 302 in the closed state. Alternatively, when the comparator circuitry 406 determines that the received signal meets or reaches the reference value, the comparator circuitry 406 may be configured to output a signal that configures the first switch 302 in the open state. The signal that is output by the comparator circuitry 406 when the received signal reaches the predetermined value may induce current through the electromagnetic device 310 (FIG. 3), which may energize or activate the electromagnetic device 310 and switch the first switch 302 (FIG. 3) to the open state.

Figure 5:
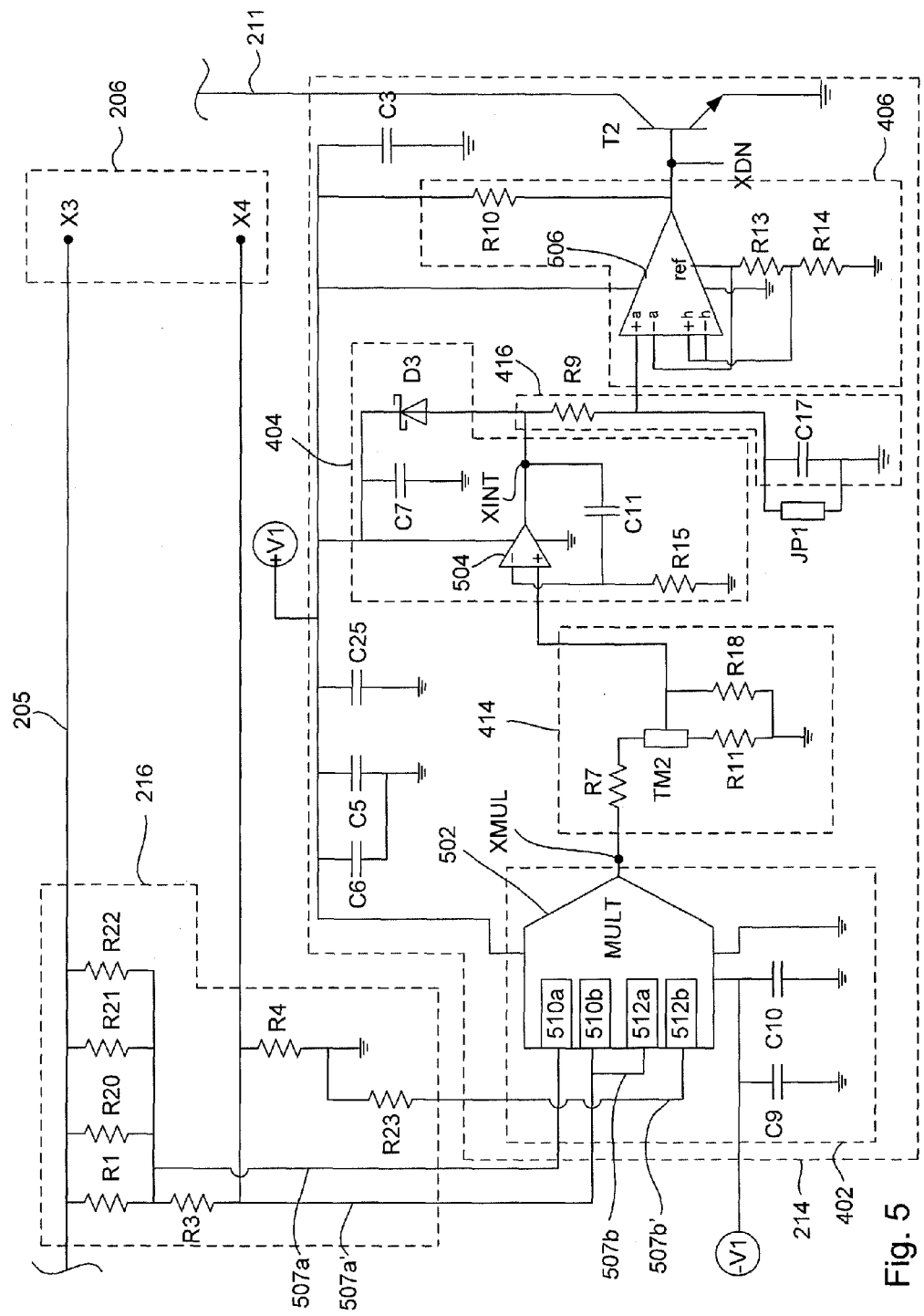
FIG. 5 shows a circuit diagram of an example circuit implementation of the energy measurement circuitry.

FIG. 5 shows a circuit schematic of an example circuit implementation of the step-down circuitry 216 and an example circuit implementation of the energy measurement circuitry 214 coupled to the output path 205 and the output 206. The step-down circuitry 216 may include a resistive network, which may include resistors R1, R3, R4, R20, R21, R22, and R23. The resistive network may be coupled to terminals X3 and X4 of the output 206 in such a way as to provide signals scaled down from the output path 205 that are proportional to the voltage and current being supplied to the medical device 106 to the energy measurement circuitry 214.

In the example circuit implementation shown in FIG. 5, the resistors R1, R3, R20, R21, and R22 may be configured as a voltage divider, that may yield a first voltage drop by resistors R1, R20, R21, and R22, which may be coupled to the output path 205 and connected in parallel, and may also yield a second voltage drop by resistor R3, which may be connected to the parallel connection of R1, R20, R21, and R22. A first voltage signal generated by the first voltage drop may be sent to the energy measurement circuitry 214 via connection 507a. A second voltage signal generated by the second voltage drop may be sent to the energy measurement circuitry 214 via connection 507a'. The first and second voltage signals may form a differential voltage signal that is received by the energy measurement circuitry 214, and that is indicative of representative of, and/or proportional to the voltage being supplied to the medical device. Four resistors, R1, R20, R21, R22 connected in parallel may be used to reduce or minimize heat generated in the voltage divider, although more or fewer than four resistors may be used.

Resistor R4 may be configured to generate a pair of signals on connections 507b and 507b', forming a differential signal that is proportional to the current being supplied to the medical device 106. The resistor R23 may be included to match input impedances of the multiplier circuitry 402. The signal generated on 507b' may have a voltage that is the voltage drop yielded by resistor R4

An example multiplier may be an Analog Devices AD835 4-Quadrant Multiplier, although other multipliers may be used. The multiplier 502 may have a pair of differential inputs, including a first differential input 510a, 510b to receive the differential voltage signal via connections 507a, 507a', and a second differential input 512a, 512b to receive the differential current signal via connections 507b, 507b'. The multiplier 510 may be configured to multiply the differential voltage signal with the differential current signal to generate an output signal indicative of and/or proportional to the instantaneous RF power being supplied to the medical device 106. The multiplier 510 may output the output signal to the integration circuitry 404 at the output XMUL.

As shown in FIG. 5, the multiplier 502 may receive power, such as positive voltage +V1 and negative voltage −1V, from the power supply circuitry 220. Capacitors C5, C6, C9, C10, and C25 may be included to reduce noise.

The output XMUL of the multiplier circuitry 402 may be coupled to the integrator circuitry 404 via connection 414. The connection 414 may include a voltage divider that is configured to scale down the output of the multiplier circuitry 402. The voltage divider may include a resistor R7, a variable resistor (or a trimmer resistor or a potentiometer) TM2, and resistors R11 and R18. The variable resistor TM2 may be configured to scale down the output of the multiplier circuitry 402 at XMUL in a range of about 25% to 50%, although other ranges are possible. The variable resistor TM2 may provide the voltage divider with variable scalability to calibrate the energy measurement circuitry 214 as a whole. The resistor R18 may be included to draw a relatively small amount of current through a wiper component of the variable resistor TM2 to reduce or minimize oxide accumulation or build up.

The integrator circuitry 404 may include an operational amplifier (op-amp) 504, which may be configured as a non-inverting op-amp integrator. An example op-amp 504 may be a National Semiconductor LM6211 low noise rail-to-rail (RRO) operation amplifier. The integrator circuitry 404 may include a resistor R15 in conjunction with a feedback capacitor C11 may determine a resistor-capacitor (RC) time constant that, in turn, determines an integration gain constant of the integration circuitry 404.

The integrator circuitry 404 may further include reset circuitry, which may include a diode D3, such as a Schottky diode, that provides a discharge path for charge stored across the capacitor C11 to discharge. When the power supply circuitry 220 (FIG. 2) is no longer supplying power to the other components of the control unit 102 (e.g., because the physician or operator removed his/her foot from the RF generator 104 and the RF generator 104 is no longer supplying RF energy to the power supply circuitry 220), the diode D3 may become forward biased, and charge stored at the output XINT may discharge through the diode D3 to the connection 514, and to the power supply circuitry 220. A capacitor C7 may be included to reduce noise.

The integrator circuitry 404 may output the signals to the comparator circuitry 406 via connection 416. In the example circuit implementation shown in FIG. 5, the connection 416 may include a low-pass filter having a resistor R9 connected with a capacitor C17, to reduce noise before the signals are supplied to the comparator circuitry 406.

The comparator circuitry 406 may receive the signals from the connection 416 and, based on the levels of the received signals, determine whether the RF energy being supplied to the medical device 106 has reached the threshold level. The comparator circuitry 406 may include a comparator 506 which may be a packaged chip or component and be powered by the positive power supply signal +V1. An example comparator 506 may be a National Semiconductor LMP7300 micropower precision comparator, although other types of comparators may be used. The comparator 506 may include a reference terminal "ref," which may set or provide a reference level or value for the comparator 506. The reference terminal "ref" may be connected or tied to a negative input terminal –a of the comparator 506.

In operation, when the level of the signals received at a positive input terminal +a reaches the reference level at the negative input terminal –a, the comparator 506 may be configured to generate an output signal at an output XDN (if the comparator 506 has an open collector or similar output). A resistor R10 may be included at the output XDN to generate a logic "high" signal. The output signal generated by the comparator 506 may be applied to a switch T2, which turns the switch T2 from an "off" state to an "on" state. The switch T2 may have a terminal connected to the connection 211 (FIG. 2), which is connected to the terminal A1 of the electromagnetic device 310. Turning switch T2 "on" may switch the first switch 302 from the closed state to the open state. In some example configurations, the switch T2 may be a semiconductor device, such as a transistor. An example transistor may be a NZT7053 NPN Darlington transistor.

The comparator 506 may further include hysteresis inputs +h, –h. The hysteresis inputs +h, –h may provide hysteresis functionality to the comparator 506 to prevent the comparator 506 from providing a fluctuating output once the comparator 506 outputs a signal to turn the switch T2 "on." Resistors R13 and R14 may be used to set the hysteresis value.

In some example circuit implementations, the energy measurement circuitry 214 may further include a jumper JP1 connected in parallel with the capacitor C17. The jumper JP1 may be configured in the energy measurement circuitry 214 such that if the jumper JP1 is shorted, the capacitor C17 may be shorted, which may prevent signals output from the integrator circuitry 404 and/or transmitted via the connection 416 from being received by the comparator circuitry 406. Shorting the jumper JP1 may allow a user or operator to perform one or more calibrations or activities on the control unit 102, such as calibration of the backup timer circuitry 218.

Table 1 provides exemplary component values for the circuit components of the circuitry implementations of the step-down circuitry 216 and the energy measurement circuitry 214 shown in FIG. 5.

TABLE 1

| R1 | 5.1 kΩ |
|---|---|
| R3 | 50 Ω |
| R4 | 1 Ω |
| R20 | 5.1 kΩ |
| R21 | 5.1 kΩ |
| R22 | 5.1 kΩ |
| R23 | 47 Ω |
| C9 | 1 µF |
| C10 | .01 µF |
| R7 | 75 Ω |
| TM2 | 50 Ω |
| R11 | 27 Ω |
| R18 | 1.5 kΩ |
| R15 | 20 kΩ |
| C11 | 2.2 µF |
| C7 | 0.1 µF |
| R9 | 10 kΩ |
| C17 | 0.1 µF |
| R13 | 300 Ω |
| R14 | 2.2 kΩ |
| R10 | 10 kΩ |
| C6 | 1 µF |
| C5 | 0.01 µF |
| C25 | 0.1 µF |
| C3 | 0.1 µF |

Figure 6:
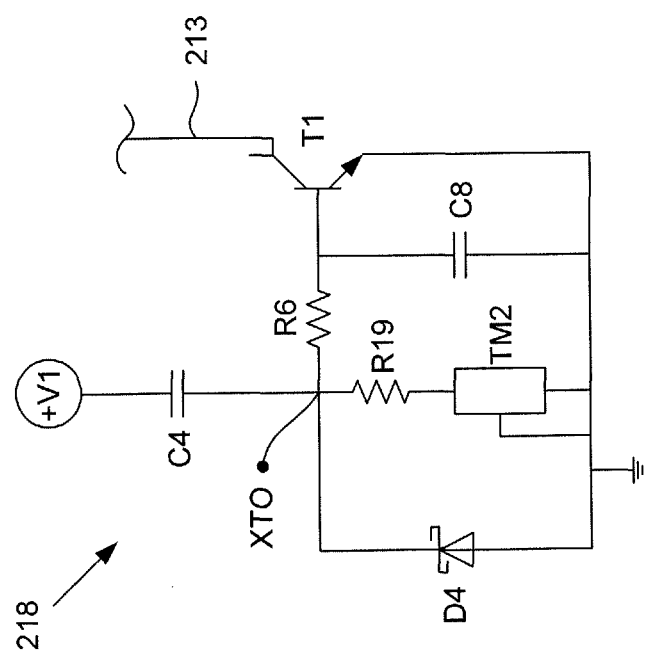
FIG. 6 shows a circuit diagram of an example circuit implementation of backup timer circuitry in the control unit.

FIG. 6 shows a circuit schematic diagram of an example circuit implementation of the backup timer circuitry 218. The backup timer circuitry 218 may include a capacitor C4 connected to a parallel connection including a resistor R19, a variable resistor TM2, a resistor R6, and a base-emitter junction of a transistor T1. As previously described, the backup timer circuitry 218 may be configured to switch the switching circuitry 204 from the closed state to the open state when a period of time elapses. In the example circuit implementation shown in FIG. 6, the period of time may be determined by a resistor-capacitor (RC) time constant set by a capacitance of the capacitor C4 and an impedance of the parallel connection of R19 and TM2 with R6 and the base-emitter junction of T1. In one example configuration, the transistor T1 may be a NZT7053 NPN Darlington transistor, although other types of transistors may be used. The variable resistor TM2 may be used, rather than a resistor with a fixed resistance, in order to provide an adjustable impedance for calibration. The collector of the transistor T1 may be coupled to the electromagnetic device 315 of the second switch 304 (FIG. 3) via the connection 213.

The example circuit implementation of the backup timer circuitry 218 may further include a capacitor C8 coupled to the base of the transistor T1 and ground. The capacitor C8 may be included to reduce noise generated in the backup timer circuitry 218. The backup timer circuitry 218 may also include a diode D4, such as a Schottky diode, connected to a node connecting the capacitor C4, the resistor R19, and the resistor R6. The diode D4 may serve as a discharge path for the capacitor C4, such as when the power supply circuitry 220 is unpowered and the positive power supply signal +V1 is not being sent to the backup timer circuitry 218. Providing the diode D2 to serve as a discharge may allow the backup timer circuitry 218 to reset quickly between activations.

In operation, when the power supply circuitry 220 is unpowered and the positive power supply signal +V1 is not being supplied to the backup timer circuitry 218, there is zero volts across the capacitor C4 since any charge stored in the capacitor C4 may discharge through the diode D4 to ground. When the power supply circuitry 220 powers up, the positive power supply signal +V1 is sent to an end of the capacitor C4, supplying a voltage to the capacitor C4. At this time, the other end of the capacitor C4 (i.e., at node XTO) is also at the voltage supplied by the positive power supply signal +V1 because the capacitor C4 may not change its voltage instantaneously (i.e., the capacitor C4 has to charge for its voltage to change). The voltage supplied by the positive power supply signal +V1 may turn the transistor T1 "on," which may induce current through the electromagnetic device 315 (FIG. 3), and switch the second switch 304 to the closed state.

After the power supply circuitry 220 initially supplies the positive power supply signal +V1 to the backup timer circuitry 218, the voltage at node XTO may decay from the voltage of the positive power supply signal +V1 at a rate, such as an exponential rate, determined by the RC time constant. The voltage at node XTO may decay to a level that turns the transistor T1 "off." When the transistor T1 is "off," current is no longer induced through the electromagnetic device 315, and the second switch 304 switches to the open state.

Under typical operation of the RF generator 104, the physician or operator of the RF generator will cease output of the RF signals from the RF generator 104, such as by removing his/her foot from a foot pedal. As previously described, the RF signals from the RF generator 104 are used to power the power supply circuitry and generate the power supply signals that are supplied to the other components of the control unit 102. As such, when the output of the RF signals is ceased, the positive power supply signal +V1 is no longer supplied to the backup timer circuitry 218. At this time, any remaining or residual charge stored in the capacitor C4 may discharge through the diode D4, yielding a zero voltage drop across the capacitor C4. The backup timer circuitry 218 may then be ready to receive the positive power supply signal +V1 from the power supply circuitry 220, in which the backup timer operation may be repeated. Table 2 provides exemplary component values for the circuit components of the circuit implementation of the backup timer circuitry 218 shown in FIG. 6.

TABLE 2

| C4 | 20 µF |
|---|---|
| R19 | 1 kΩ |
| TM1 | 50 kΩ |
| R6 | 47 kΩ |
| C8 | 0.01 µF |

Figure 7:
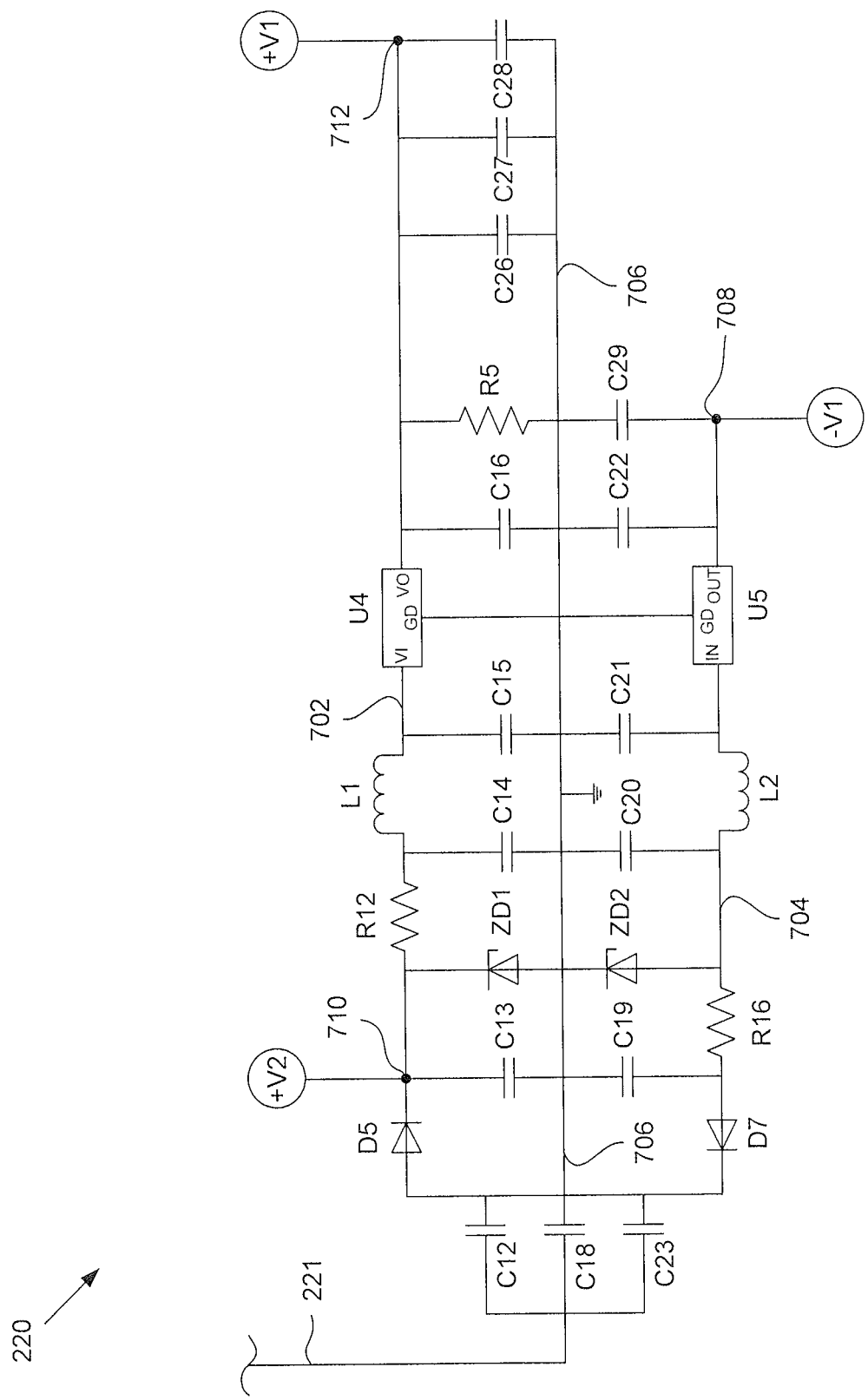
FIG. 7 shows a circuit diagram of an example circuit implementation of power supply circuitry in the control unit.

FIG. 7 shows an example circuit implementation of the power supply circuitry 220. The power supply circuitry 220 may be configured to generate and output one or more positive power supply (e.g., DC power supply) signals and/or one or more negative power supply (e.g., DC power supply) signals.

The power supply circuitry 220 may include capacitors C12, C18, and C23 coupled to the connection 221 and the first and second portion 702, 704. The capacitors C12, C18, C23 may be configured to step-down the voltage of the RF signals received from the terminal X1 via connection 221. In alternative configurations, components other than capacitors, such as resistors, may be used. The diodes D5, D7 may provide rectification, such as half-wave rectification, to convert the RF (i.e., AC) signals into rectified AC signals.

The power supply circuitry 220 may include a resistor R16 and a zener diode ZD2 to function as a generally imprecise voltage regulator to prevent the voltage generated at the node between the resistor R16, the zener diode ZD2, and an inductor L2 from damaging a voltage regulator U5. A pi network, formed by the inductor L2 and capacitors C20, C21, may reduce noise before signals are received by the voltage regulator U5. An example voltage regulator U5 may be a National Semiconductor 79L05 voltage regulator Capacitors C22 and C29 may provide further noise filtering.

A zener diode ZD1, in conjunction with the step down capacitors C12, C18, C23, may function as a generally imprecise voltage regulator for the voltage generated at node 710. A resistor R12 may be coupled to node 710 to further scale down the voltage to prevent a regulator U4 from being damaged. A pi network, formed by an inductor L1 and capacitors C14 and C15, may reduce noise before signals are received by the voltage regulator U4. The voltage regulator U4 may be configured to output a substantially regulated second positive power supply +V1 at node 712. The output of the regulator U4 may discharge through a resistor R5 after the power supply circuitry 220 powers down. Capacitors C13, C19, C16, C26, C27, and C28 may be included in the power supply circuitry 220 to further reduce noise.

Table 3 provides exemplary component values for the circuit components of the circuit implementation of the power supply circuitry 220 shown in FIG. 7.

TABLE 3

| C12 | 1 nF |
|---|---|
| C18 | 1 nF |
| C23 | 1 nF |
| D5 | RS2B |
| D7 | RS2B |
| C13 | 1 µF |
| C19 | 1 µF |
| R16 | 150 Ω |
| R12 | 200 Ω |
| C14 | 1 µF |
| C20 | 1 µF |
| L1 | 30 µH |
| L2 | 30 µH |
| C15 | 1 µF |
| C21 | 1 µF |
| U4 | MCP1703CB |
| U5 | 79L05 |
| C16 | 1 µF |
| C22 | 1 µF |
| R5 | 4.7 kΩ |
| C29 | 0.1 µF |
| C26 | 0.1 µF |
| C27 | 0.1 µF |
| C28 | 0.1 µF |

Figure 8:
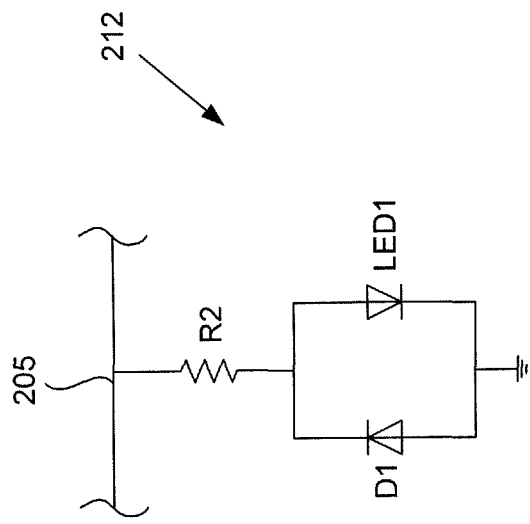
FIG. 8 shows a circuit diagram of an example circuit implementation of indication circuitry in the control unit.

FIG. 8 shows an example circuit implementation of indication circuitry 212 coupled to the output path 205. The indication circuitry 212 may include a light emitting diode LED1 that outputs a light signal or is "on" when RF energy is being supplied to the output 206. A resistor R2 controlling an amount of current supplied to LED1 may have a resistance of about 750Ω. In addition, the indication circuitry 212 may include a diode D1 connected anti-parallel to the LED 1.

The indication circuitry 212 may identify to an operator when to cease application of the RF energy. For example, the operator may remove bias on a foot pedal or other RF actuator when the LED turns from "on" to "off."

Figure 9:
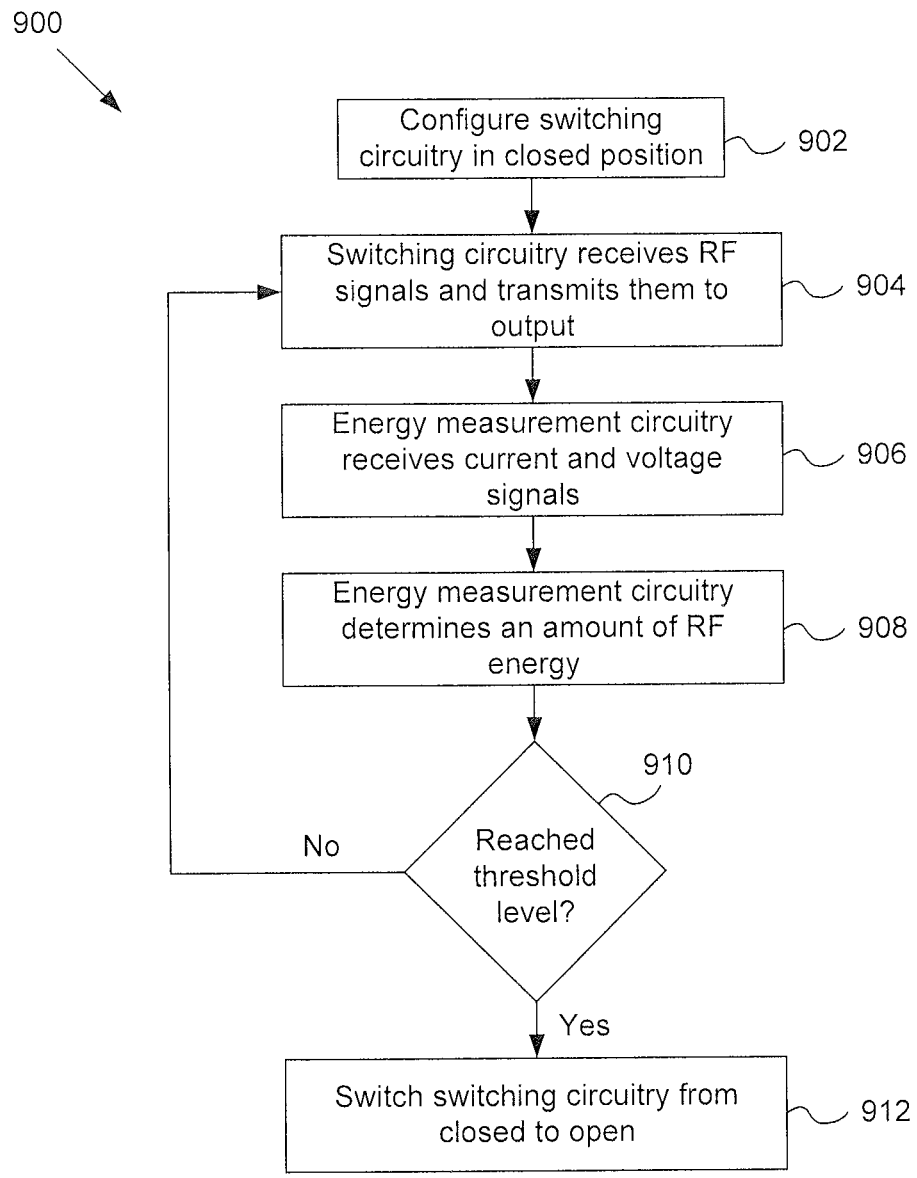
FIG. 9 shows a flow chart of an example method operating a control unit coupled to a RF generator to control transmission of RF energy to a medical device positioned at a treatment site within a patient.

FIG. 9 shows a flow chart of an example method 900 of operating a control unit coupled to a RF generator to control transmission of RF energy to a medical device positioned at a treatment site within a patient. At block 902, switching circuitry of the control unit, such as one or more relays, may be positioned or configured in a closed state. At block 904, the switching circuitry may receive the RF energy, and in the closed state, output the RF energy to an output of the control unit. At block 906, a portion of the RF energy output by the switching circuitry may be received by energy measurement circuitry of the control unit. The portion of the RF energy may be received as energy indicative or, representative of, and/or proportional to the voltage and current being supplied to the medical device.

At block 908, the energy measurement circuitry may determine an amount of RF energy, such as an amount of total energy, being output by the control unit and supplied to the medical device. At block 910, the energy measurement circuitry may determine whether the RF energy has reached a threshold level, which may be a predetermined or selected level that when exceeded (or substantially exceeded), may cause harm to the patient. If the energy measurement circuitry determines that the RF energy has not reached the threshold level, then the method may proceed back to block 904, where the switching circuitry may continue to receive RF energy from the RF generator and transmit the RF energy to the output of the control unit. Alternatively, if the energy measurement circuitry determines that the RF energy has reached the threshold level, then the method may proceed to block 912, where the energy measurement circuitry may cause the switching circuitry to switch from the closed state to an open state, such as by inducing current through an electromagnetic device of a relay in the switching circuitry.

Figure 10:
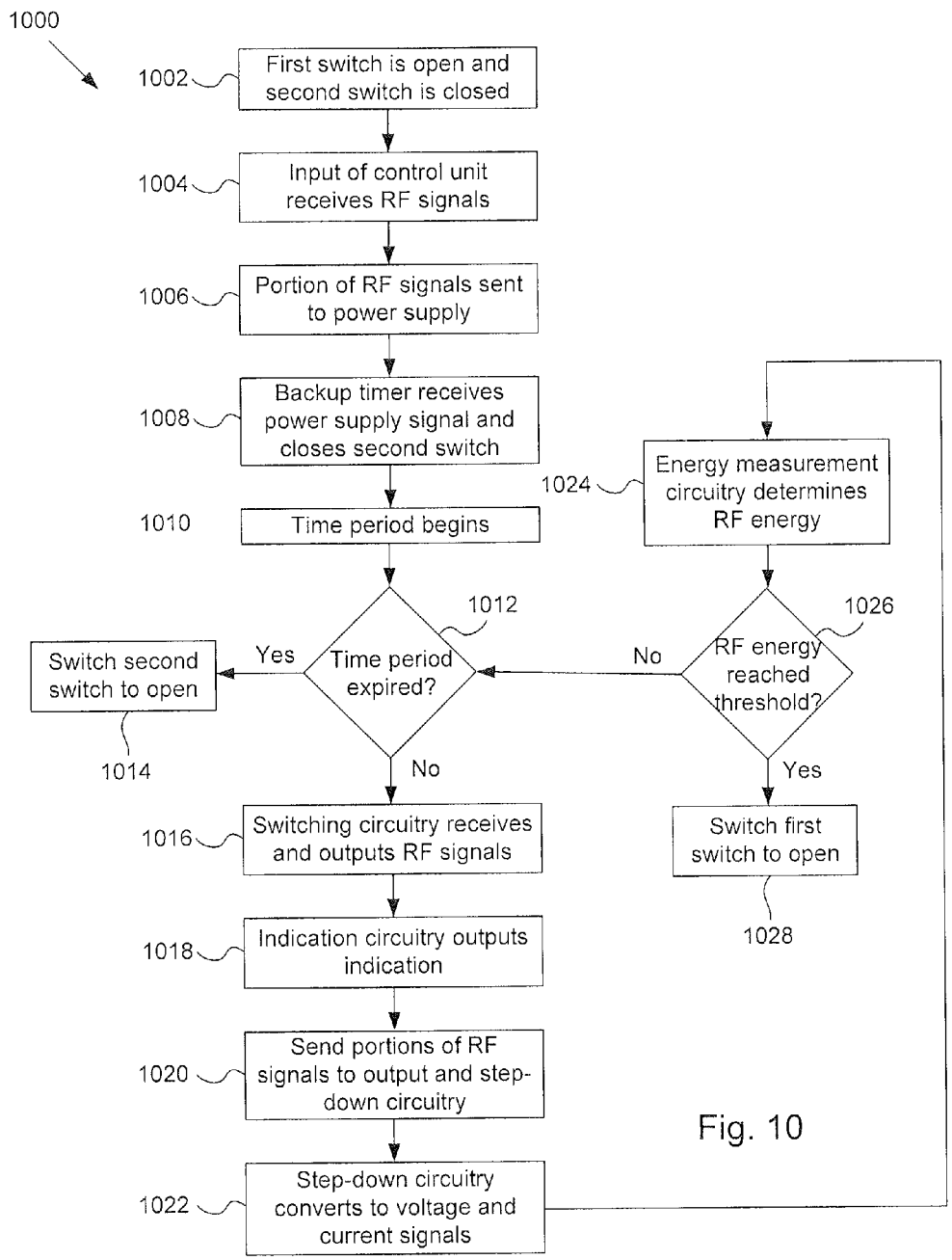
FIG. 10 shows a flow chart of an example method operating a control unit coupled to a RF generator to control transmission of RF energy to a medical device positioned at a treatment site within a patient.

FIG. 10 shows a flow chart of an alternative example method 1000 of operating a control unit coupled to a RF generator to control transmission of RF energy to a medical device positioned at a treatment site within a patient. At block 1002, a first switch of switching circuitry of the control unit may be configured in a closed state, and a second switch of the switching circuitry connected in series with the first switch may be configured in an open state. At block 1004, an input of the control unit may receive RF energy from the RF generator. At block 1006, a portion of the RF energy received by the input may be supplied to power supply circuitry of the control unit, which the power supply circuitry may use to generate one or more power supply energy.

At block 1008, backup timer circuitry of the control unit may receive a power supply signal from the power supply circuitry, and upon reception, may cause the second switch in the switching circuitry to switch from the open state to the closed state. At block 1010, a time period determined by a RC time constant in the backup timer may begin. At block 1012, the backup timer circuitry may determine if the time period has expired. If the time period as expired, then at block 1014, the backup timer may cause the second switch to switch to an open state, which may prevent RF energy output from the RF generator from being output by the control unit. Alternatively, if the timer period has not expired, then the method may proceed to block 1016.

At block 1016, a remaining portion of the RF energy that is not sent to the power supply circuitry may be sent to the switching circuitry because both the first switch and the second switch may now be configured in the closed state. Also, at block 1016, the switching circuitry may output the received RF energy along an output path to an output of the control unit. At block 1018, indication circuitry may receive a portion of the RF energy output by the switching circuitry, and in response, may output an indication, such as a light output, indicating to an operator that RF energy is being output by the control unit and supplied to the medical device. At block 1020, a portion of the RF energy that was not sent to the indication circuitry may be sent to step-down circuitry, and a remaining portion may be sent to an output of the control unit, where the remaining portion may be supplied to the medical device at a treatment site.

At block 1022, the portion sent to the step-down circuitry may be converted to signals proportional to the RF energy being supplied to the medical device. At block 1024, energy measurement circuitry may receive the signals from the step-down circuitry, and from the received signals, may determine an amount of RF energy, such as an amount of total energy, being output by the control unit and supplied to the medical device. At block 1026, the energy measurement circuitry may determine whether the RF energy has reached a threshold level. If the energy measurement circuitry determines that the RF energy has not reached the threshold level, then the method may proceed back to block 1012, where the switching circuitry may determine whether the time period has expired.

Alternatively, if the energy measurement circuitry determines that the RF energy has reached the threshold level, then the method may proceed to block 1028, where the energy measurement circuitry may cause the first switch of the switching circuitry to switch from the closed state to an open state, such as by inducing current through an electromagnetic device of a relay in the first switch, which may prevent RF energy from being output by the control unit to the medical device.

Figure 11:
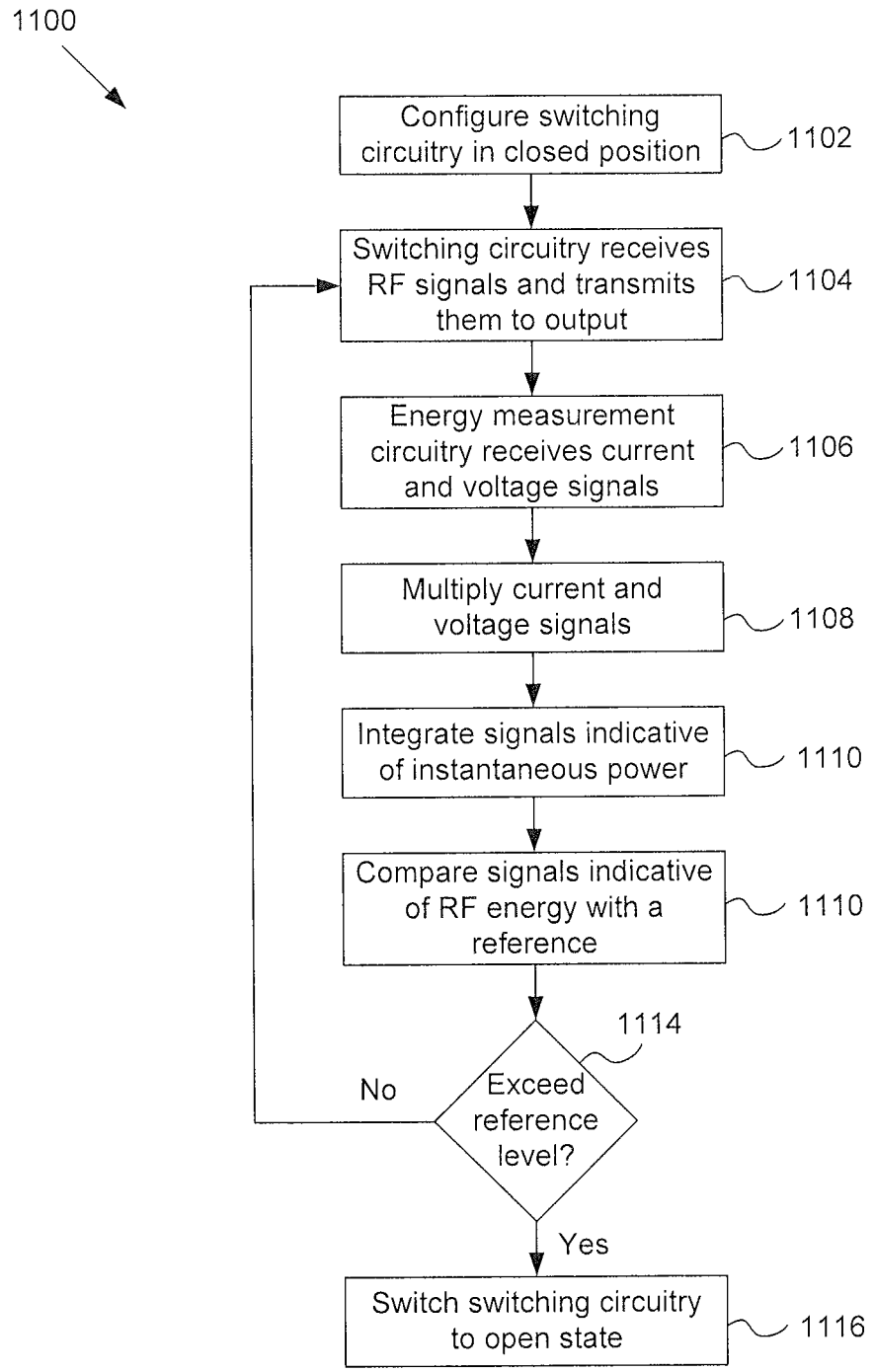
FIG. 11 shows a flow chart of an example method operating a control unit coupled to a RF generator to control transmission of RF energy to a medical device positioned at a treatment site within a patient.

FIG. 11 shows a flow chart of an alternative example method 1100 of operating a control unit coupled to a RF generator to control transmission of RF energy to a medical device positioned at a treatment site within a patient. At block 1102, switching circuitry may be configured in a closed state. At block 1104, the switching circuitry, in the closed state, may receive RF energy and transmit the received RF energy to an output of the control unit. At block 1106, a portion of the RF energy output from the switching circuitry may be sent to energy measurement circuitry as signals indicative of voltage and current being supplied to the medical device.

At block 1108, a multiplier of the energy measurement circuitry may multiply signals indicative of the voltage with signals indicative of the current, and generate a signal indicative of the instantaneous power being supplied to the medical device. At block 1110, an integrator of the energy measurement circuitry may integrate the signals indicative of the instantaneous power and generate signals indicative of the total energy being supplied to the medical device. At block 1112, a comparator of the energy measurement circuitry may compare the signals indicative of the or total energy with a reference value. At block 1114, the comparator may determine whether the signals indicative of the total energy have exceeded a reference level. If the reference level is not exceeded, then the method may proceed back to block 1104. Alternatively, if the reference level is not exceeded, then at block 1116, the comparator may output a signal that causes the switching circuitry to switch from the closed state to the open state, preventing RF energy from being output from the control unit to the medical device.

Figure 12:
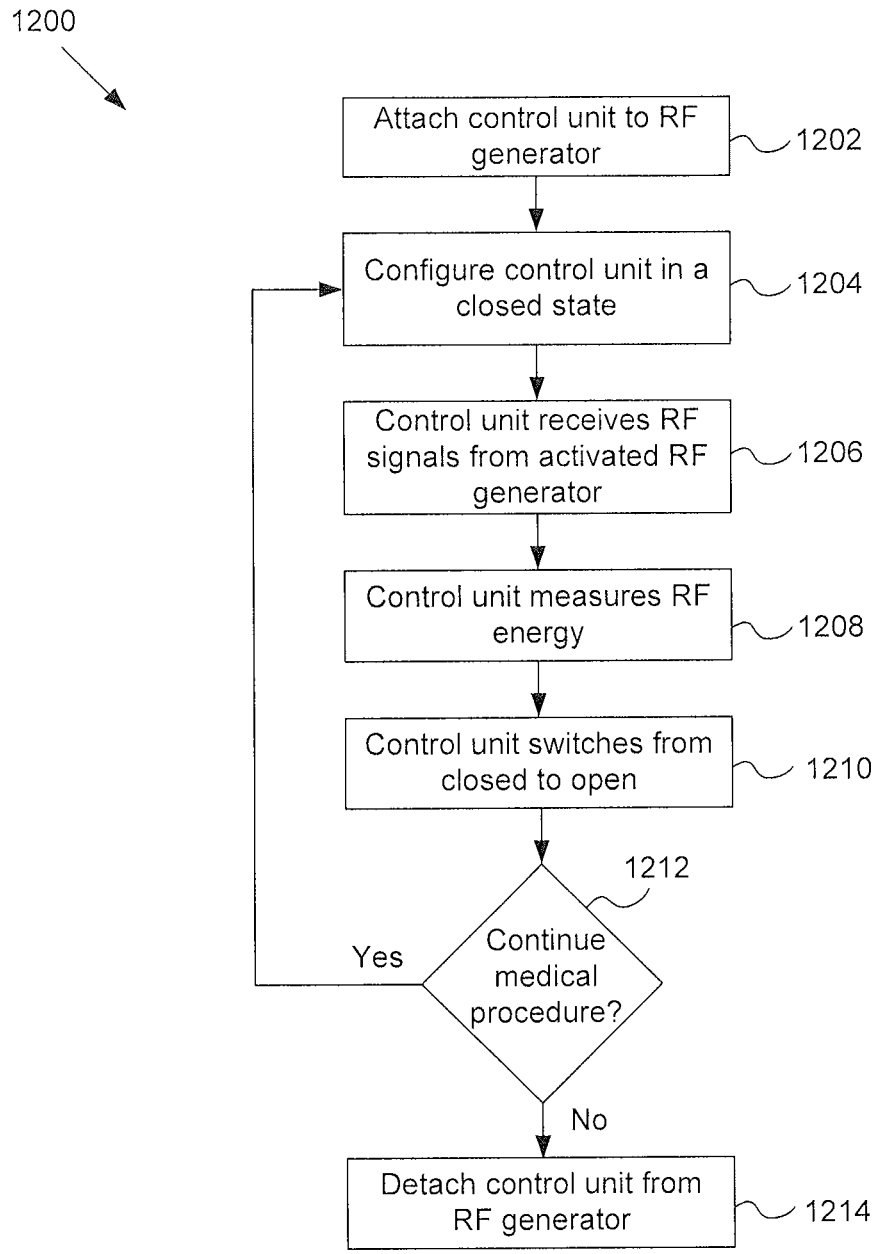
FIG. 12 shows a flow chart of an example method operating a control unit coupled to a RF generator to control transmission of RF energy to a medical device positioned at a treatment site within a patient.

FIG. 12 shows a flow chart of an alternative example method 1200 of operating a control unit in conjunction with a RF generator to control transmission of RF energy to a medical device positioned at a treatment site within a patient during a medical procedure. At block 1202, an input of the control unit may be coupled to an output of the RF generator. At block 1204, the control unit may be configured in a closed state. At block 1206, the RF generator may be activated and the control unit may receive RF energy from the RF generator and output the RF energy to a medical device at the treatment site. At block 1208, the control unit may measure the RF energy being supplied to the medical device. At block 1210, the control unit may switch from the closed state to the open state when the control unit detects that the RF energy being supplied to the medical device has reached a threshold level. At block 1212, if more RF energy is to be supplied to the treatment site, then the method may proceed back to block 1204, where the control unit may be configured in the closed state. Alternatively, if no more RF energy is to be supplied to the treatment site, then the method may proceed to block 1214, where the medical procedure has ended and the control unit may be detached from the RF generator.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A control unit that is configured to control delivery of radio frequency (RF) energy to a medical device, the control unit comprising:
   an input terminal configured to receive RF energy from an RF generator;
   switching circuitry configured to switch between a closed state and an open state,
      wherein when the switching circuitry is configured in the closed state, the switching circuitry is configured to permit a first portion of the RF energy received from an RF generator to be output by the control unit to a medical device; and
      wherein when the switching circuitry is configured in the open state, the switching circuitry is configured to prevent the first portion of the RF energy from being output by the control unit to the medical device;
   energy measurement circuitry configured to:
      measure an amount of the first portion of the RF energy delivered to the medical device; and
      switch the switching circuitry from the closed state to the open state when the amount of the first portion of the RF energy delivered to the medical device reaches a predetermined RF energy level; and
   power supply circuitry configured to:
      receive a second portion of the RF energy received from the RF generator;
      generate one or more power supplies based on the second portion of the RF energy; and
      supply the one or more power supplies to the energy measurement circuitry to power the energy measurement circuitry.

2. The control unit of claim 1, further comprising an input connector configured to be coupled to an output of the RF generator and receive the RF energy from the output of the RF generator.

3. The control unit of claim 2, wherein the input connector is configured to be removably attached to the output of the RF generator.

4. The control unit of claim 1, wherein the control unit is configured to connect to a bipolar output of the RF generator.

5. The control unit of claim 1, wherein the energy measurement circuitry comprises:
   multiplier circuitry configured to:
      multiply a first signal indicative of voltage delivered to the medical device with a second signal indicative of current delivered to the medical device, the multiplication being indicative of instantaneous power being delivered to the medical device.

6. The control unit of claim 5, wherein the energy measurement circuitry further comprises integrator circuitry in communication with the multiplier circuitry, the integrator configured to:
   receive a third signal indicative of the instantaneous power delivered to the medical device; and
   integrate the third signal, the integration being indicative of an amount of the first portion of the RF energy delivered to the medical device.

7. The control unit of claim 6, wherein the energy measurement circuitry further comprises: comparator circuitry in communication with the integrator circuitry, the comparator circuitry configured to:
   receive a fourth signal indicative of the amount of the first portion of the RF energy delivered to the medical device; and
   compare the fourth signal with a reference level to determine whether the amount of the first portion of the RF energy has reached a threshold energy level; and
   upon determination that the amount of the first portion of the RF energy has reached the threshold energy level, generate a fifth signal that causes the switching circuitry to switch from the closed state to the open state.

8. The control unit of claim 1, wherein the switching circuitry comprises a relay configured to switch from a closed state to an open state when the amount of the first portion of the RF energy delivered to the medical device reaches the predetermined RF energy level.

9. The control unit of claim 1, wherein the switching circuitry further comprises a first switch connected in series with a second switch, wherein the first switch is configured to switch from a closed state to an open state when the amount of the first portion of the RF energy reaches the predetermined energy level, and wherein the second switch is configured to switch from the closed state to the open state in response to an elapsed predetermined period of time.

10. The control unit of claim 1, wherein the control unit comprises a housing separate from and housing of the RF generator.

11. A method to control transmission of radio frequency (RF) energy from a RF generator to a medical device with a control unit coupled to the RF generator and the medical device, the method comprising:
   configuring switching circuitry of the control unit in a closed state;
   receiving, at an input of the control unit, the RF energy from the RF generator;
   when the switching circuitry is in the closed state:
      receiving, with the switching circuitry, a first portion of the RF energy; and
      transmitting, with the switching circuitry, the first portion of the RF energy to an output of the control unit;
   determining, with energy measurement circuitry, an amount of the first portion of the RF energy delivered to the medical device;
   switching the switching circuitry, from the closed state to an open state in response to determining that the amount of the first portion of the RF energy reached a predetermined threshold energy level;

receiving, with power supply circuitry of the control unit, a second portion of the RF energy;

generating, with the power supply circuitry, one or more power supplies based on the second portion of the RF energy; and supplying, with the power supply circuitry, the one or more power supplies to the energy measurement circuitry to power the energy measurement circuitry.

12. The method of claim 11, further comprising:

coupling an input of the control unit to an output of the RF generator prior to a medical procedure being performed at a treatment site within a patient using the medical device; and decoupling the input of the control unit from the output of the RF generator after the medical procedure is performed.

13. The method of claim 11, further comprising:

generating, with step-down circuitry, a first signal indicative of voltage delivered to the medical device and a second signal indicative of current delivered to the medical device based on the first portion of the RF energy; and wherein determining, with the energy measurement circuitry, the amount of the first portion of the RF energy delivered to the medical device comprises:

multiplying, with multiplier circuitry, the first signal and the second signal; the multiplication indicative of instantaneous power delivered to the medical device.

14. The method of claim 13, wherein determining, with the energy measurement circuitry, the amount of the first portion of the RF energy delivered to the medical device further comprises:

integrating, with integrator circuitry, signals indicative of the instantaneous power that were generated from the multiplication by the multiplier circuitry, the integration indicative of the amount of the first portion of the RF energy delivered to the medical device.

15. The method of claim 14, further comprising:

comparing, with comparator circuitry, a third signal indicative of the first amount of the first portion of the RF energy with a reference level, the third signal generated from the integration by the integrator circuitry, the reference level indicative of the predetermined threshold energy level; and determining, with the comparator circuitry, that the third signal reached the reference level, the determination being based on the comparison, wherein switching the switching circuitry from the closed state to the open state comprises switching the switching circuitry from the closed state to the open state upon determining with the comparator circuitry that the third signal reached the reference level.

16. A control unit configured to control delivery of radio frequency (RF) energy, the control unit comprising:

an output coupled to a medical device configured to perform an ablation procedure;

an input coupled to an output of a RF generator configured to supply RF energy to the medical device for the ablation procedure;

switching circuitry coupled to the input and the output, the switching circuitry configured to permit the control unit to output a first portion of the RF energy received from the RF generator in a closed state, and to prevent the control unit from outputting the first portion of the RF energy received from the RF generator in an open state; and energy measurement circuitry coupled to the output, the energy measurement circuitry configured to determine an amount of the first portion of the RF energy being delivered to the medical device, and to switch the switching circuitry from the closed state to the open state when the amount of first portion of the RF energy reaches a threshold level; and power supply circuitry configured to:

receive a second portion of the RF energy received from the RF generator;

generate one or more power supplies based on the second portion of the RF energy received from the RF generator; and supply the one or more power supplies to active components of the control unit.

17. The control unit of claim 16, wherein the control unit comprises a housing that is outside a housing of the RF generator when the input of the control unit is coupled to the output of the RF generator.

18. The control unit of claim 16, wherein the energy measurement circuitry comprises:

analog multiplier circuitry configured to multiply signals indicative of voltage delivered to the medical device with signals indicative of current delivered to the medical device;

analog integrator circuitry configured to integrate signals generated from the multiplication, the integration indicative of the RF energy delivered to the medical unit.

* * * * *